United States Patent [19]

Delaney

[11] Patent Number: 4,963,539
[45] Date of Patent: Oct. 16, 1990

[54] PHOSPHONATE AND PHOSPHONAMIDE ENDOPEPTIDASE INHIBITORS

[75] Inventor: Norma G. Delaney, Princeton, N.J.

[73] Assignee: E. R. Squibb & Sons, Inc., Princeton, N.J.

[21] Appl. No.: 298,550

[22] Filed: Jan. 17, 1989

Related U.S. Application Data

[63] Continuation-in-part of Ser. No. 223,121, Jul. 22, 1988, abandoned, which is a continuation-in-part of Ser. No. 95,065, Sep. 10, 1987, abandoned.

[51] Int. Cl.$^5$ .................... A61K 31/66; C07F 9/09
[52] U.S. Cl. ............................ 514/119; 558/170; 558/171
[58] Field of Search ................ 558/170, 171; 514/119

[56] References Cited

U.S. PATENT DOCUMENTS

| | | | |
|---|---|---|---|
| 4,432,971 | 2/1984 | Karanewsky et al. | 424/177 |
| 4,432,972 | 2/1984 | Karanewsky et al. | 424/177 |
| 4,452,790 | 6/1984 | Karanewsky et al. | 424/200 |
| 4,616,005 | 10/1986 | Karanewsky et al. | 514/80 |
| 4,749,688 | 6/1988 | Haslanger et al. | 514/19 |
| 4,853,476 | 8/1989 | Petrakis et al. | 558/170 |

FOREIGN PATENT DOCUMENTS

890948 2/1982 Belgium .
117429 9/1984 European Pat. Off. .

OTHER PUBLICATIONS

Bartlett et al., "Phosphonamidates As Transition-State Analogue Inhibitors of Thermolysin, Biochemistry," vol. 22, p. 4618–4624 (1983).

Bartlett et al., "An Anaysis Of The Enzyme Inhibitor Binding Interactions . . . Thermolysin, Phosphorus and Sulfur," vol. 30, p. 537–543 (1987).

*Primary Examiner*—Cecilia Shen
*Attorney, Agent, or Firm*—Stephen B. Davis

[57] ABSTRACT

Compounds of the formula

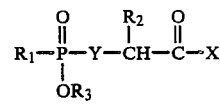

wherein Y is O or NH and X is

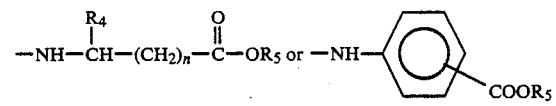

will inhibit the action of neutral endopeptidase. As a result, such compounds produce diuresis, natriuresis, and lower blood pressure as well as being useful in the treatment of congestive heart failure, relieving pain, and diarrhea when administered to a mammalian host.

13 Claims, No Drawings

PHOSPHONATE AND PHOSPHONAMIDE ENDOPEPTIDASE INHIBITORS

PRIOR APPLICATIONS

This application is a continuation-in-part of Ser. No. 223,121 filed July 22, 1988, now abandoned which in turn was a continuation-in-part of Ser. No. 95,065 filed Sept. 10, 1987, now abandoned.

BACKGROUND OF THE INVENTION

Karanewsky et al. in U.S. Pat. Nos. 4,452,790 and 4,616,005 disclose that phosphonate compounds including those of the formula

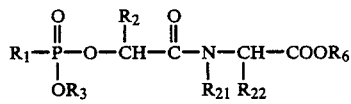

possess angiotensin converting enzyme inhibition activity and thus are useful as hypotensive agents.

Karanewsky et al. in U.S. Pat. No. 4,432,972 disclose that phosphonamide compounds including those of the formula

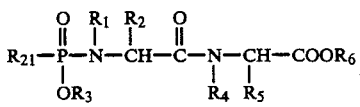

possess angiotensin converting enzyme inhibition activity and enkephalinase inhibition activity. Thus, these compounds are useful as hypotensive and analgesic agents.

Delaney et al. in U.S. Ser. No. 59,072 filed June 8, 1987 disclose that the phosphonate compounds of Karanewsky et al. U.S. Pat. Nos. 4,452,790 and 4,616,005 and the phosphonamide compounds of Karanewsky et al. U.S. Pat. No. 4,432,972 described above are neutral endopeptidase inhibitors and will produce diuresis, natriuresis, and reduce blood pressure.

Gaeta in European Patent Application No. 117,429 discloses phosphorus containing enkephalinase inhibitors of the formula

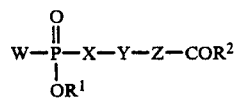

wherein W is $R^1$ or $OR^1$, X is $-(CH_2)_p-CHR^3$ or $-CHR^3-(CH_2)_p-$, Y is

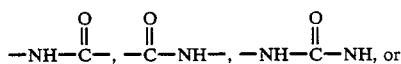

Z is o-, m-, p-phenylene, or $-(CHR^4)_r$, r is 1, 2, 3 or 4, and $R^4$ includes hydrogen, alkyl, alkoxy, cycloalkyl, cycloalkylmethyl, 3-indolylmethyl, hydroxymethyl, $-CH_2-CH_2-S-CH_3$, phenyl, substituted phenyl, benzyl, substituted benzyl, etc.

Table A shows the following compounds

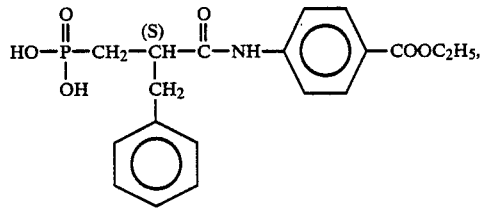

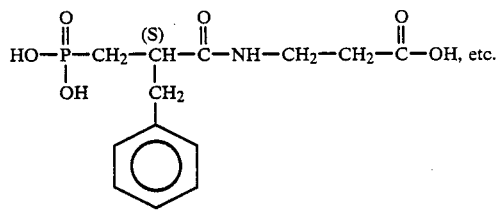

SUMMARY OF THE INVENTION

This invention is directed to the new phosphonates and phosphonamides of formula I and salts thereof

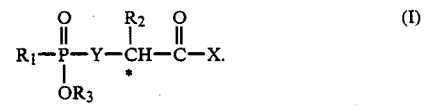

X is

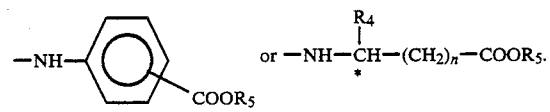

Y is NH or O.

$R_2$ and $R_4$ are independently selected from hydrogen, lower alkyl, halo substituted lower alkyl,

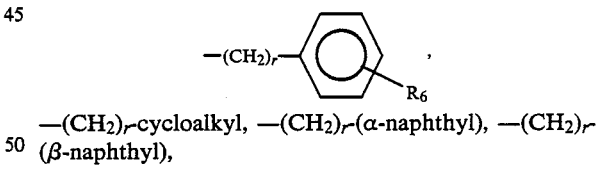

$-(CH_2)_r$-cycloalkyl, $-(CH_2)_r$-($\alpha$-naphthyl), $-(CH_2)_r$-($\beta$-naphthyl),

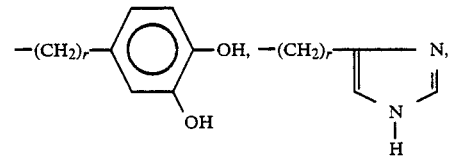

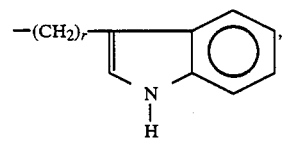

$-(CH_2)_r-NH_2$, $-(CH_2)_r-SH$, $-(CH_2)_r$-S-lower alkyl,

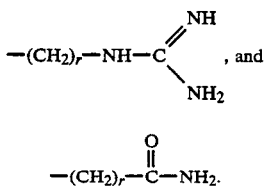

$R_1$ is alkyl of 1 to 10 carbons,

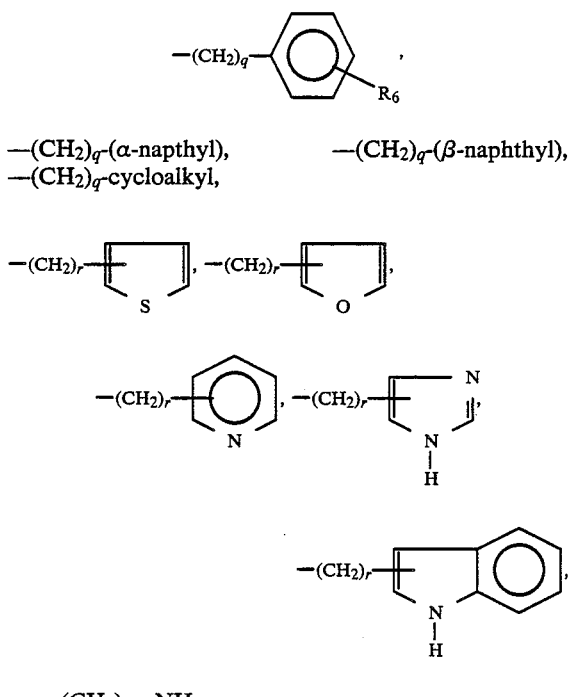

or —$(CH_2)_p$—$NH_2$.

$R_6$ is hydrogen, lower alkyl of 1 to 4 carbons, lower alkoxy of 1 to 4 carbons, lower alkylthio of 1 to 4 carbons, halo, hydroxy, $CF_3$, phenyl,

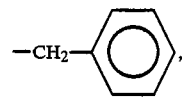

or 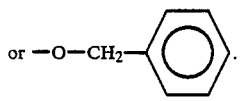

$R_3$ and $R_5$ are selected from hydrogen, lower alkyl, benzyl, benzhydryl, a salt forming ion, and

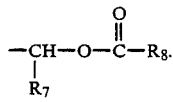

$R_7$ is hydrogen, lower alkyl, cycloalkyl, or phenyl.
$R_8$ is hydrogen, lower alkyl, lower alkoxy, or phenyl.
r is an integer from 1 to 4.
q is zero or an integer from 1 to 7.
p is an integer from 1 to 7.
n is an integer from 1 to 9.

DETAILED DESCRIPTION OF THE INVENTION

This invention in its broadest aspects relates to the phosphonate and phosphonamide compounds of formula I above, to compositions containing such compounds, to the method of using such compounds in the treatment of hypertension, congestive heart failure, renal failure, or hepatic cirrhosis and to the method of using such compounds as analgesic or antidiarrheal agents.

The term alkyl used in defining $R_1$ refers to straight or branched chain hydrocarbon radicals having up to ten carbons, for example, methyl, ethyl, propyl, isopropyl, butyl, isobutyl, t-butyl, pentyl, isopentyl, heptyl, octyl, decyl, etc. The term lower alkyl used in defining various symbols refers to straight or branched chain radicals having up to seven carbons. The preferred alkyl and lower alkyl groups are straight or branched chain of up to four carbons. Similarly the terms lower alkoxy and lower alkylthio refer to such lower alkyl groups attached to an oxygen or sulfur.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

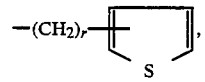

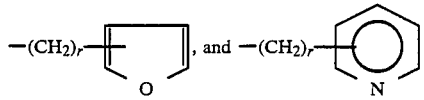

represent that the alkylene bridge is attached to an available carbon atom.

The compounds of formula I wherein Y is O, X is $$-NH-\overset{R_4}{\underset{|}{CH}}-(CH_2)_n-COOR_5,$$

and $R_1$ is other than —$(CH_2)_p$—$NH_2$ can be prepared by coupling a phosphonochloridate of the formula

to the hydroxyacyl amino acid ester of the formula

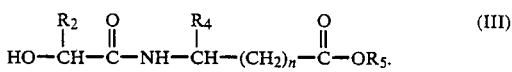

Alternatively, these compounds can also be prepared by coupling a phosphonous acid of the formula

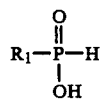  (IV)

to the hydroxyacyl amino acid ester of formula III to give the phosphonous ester of the formula

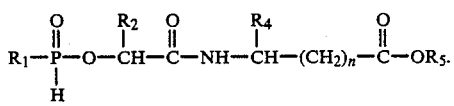  (V)

Preferably, the above reactions are performed in the presence of a catalytic amount of (N,N-dimethylamino)pyridine or 4-pyrrolidinopyridine.

Treatment of a solution of the phosphonous ester of formula V with an oxidizing agent such as sodium periodate gives the desired monoester product of formula I, i.e., $R_3$ is hydrogen.

Of course, the $R_5$ ester group as well as the $R_3$ ester group in the above procedure can be removed by conventional means to give the desired products wherein $R_3$ and $R_5$ are both hydrogen.

The compounds of formula I wherein Y is —NH, X is

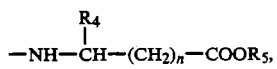

and $R_1$ is other than —$(CH_2)_p$—$NH_2$ can be prepared by coupling the phosphonochloridate of formula II to the dipeptide ester of the formula

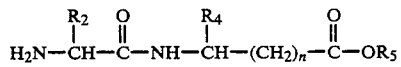

particularly as the hydrochloride salt. Again, the $R_3$ and $R_5$ ester groups can be removed to give the final products in acid form.

The compounds of formula I wherein Y is O, X is

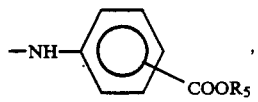

and $R_1$ is other than —$(CH_2)_p$—$NH_2$ can be prepared by coupling the phosphonochloridate of formula II to the hydroxyacyl aminobenzoic acid ester of the formula (VII)

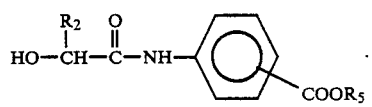

Again, the $R_3$ and $R_5$ ester groups can be removed to give the final products in acid form.

Alternatively, these compounds can also be prepared by coupling the phosphonous acid of formula IV to the hydroxyacyl aminobenzoic acid ester of formula VII to give the phosphonous ester of the formula

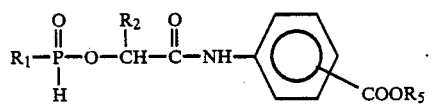  (VIII)

Treatment of a solution of the phosphonous ester of formula VIII with an oxidizing agent such as sodium periodate gives the desired monoester product of formula I, i.e., $R_3$ is hydrogen.

The compound of formula I wherein Y is —NH, X is

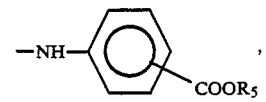

and $R_1$ is other than —$(CH_2)_p$—$NH_2$ can be prepared by coupling the phosphonochloridate of formula II to the aminobenzoic acid ester compound of the formula

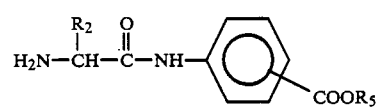  (IX)

particularly as the hydrochloride salt. Again, the $R_3$ and $R_5$ ester groups can be removed to give the final products in acid form.

The compounds of formula I wherein $R_1$ is —$(CH_2)_p$—$NH_2$ can be prepared by coupling a phthalidyl protected phosphonochloridate of the formula

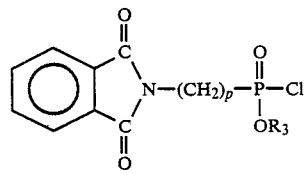  (X)

to the hydroxyacyl amino acid ester of formula III, to the dipeptide ester of formula VI, to the hydroxyacyl aminobenzoic acid ester of formula VII, or to the aminobenzoic acid ester compound of formula IX, preferably wherein $R_5$ is benzyl. Treatment with hydrazine removes the phthalidyl protecting group and the $R_3$ and $R_5$ ester group can also be removed.

The phosphonochloridates of formula II are prepared by known procedures. For example, treatment of a phosphonate of the formula

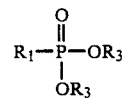  (XI)

with phosphorus pentachloride gives the desired phosphonochloridates. Preparation of the phthalidyl protected phosphonochloridate of formula X is described by Karanewsky et al. in U.S. Pat. Nos. 4,432,971 and 4,432,972.

The hydroxyacyl amino acid ester reagents of formula III can be prepared by treating an amino acid of the formula

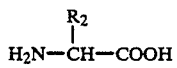

(XII)

with sulfuric acid and sodium nitrite to give the carboxylic acid

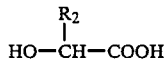

(XIII)

which is then coupled with the amino acid ester of the formula

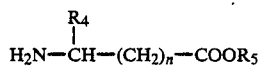

(XIV)

according to known techniques. For example, the reaction can be performed in the presence of a coupling agent such as dicyclohexylcarbodiimide.

Similarly, the dipeptide ester reagents of formula VI can be prepared by coupling an N-protected form of the amino acid of formula XII and the amino acid ester of formula XIV according to known techniques followed by removal of the N-protecting group.

The hydroxyacyl aminobenzoic acid ester reagent of formula VII can be prepared by reacting the carboxylic acid of formula XIII with the desired aminobenzoic acid ester. Similarly, the aminobenzoic acid ester compound of formula IX can be prepared by coupling an N-protected form of the amino acid of formula XII and the desired aminobenzoic acid ester according to known techniques followed by removal of the N-protecting group.

In the above reactions if $R_2$ and/or $R_4$ is

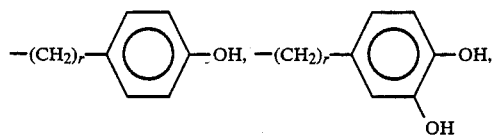

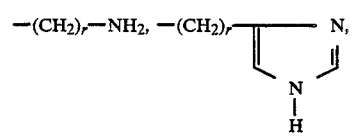

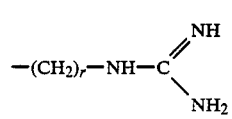

then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The products of formula I wherein either or both of $R_3$ and $R_5$ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_3$ and $R_5$ are hydrogen.

The ester products of formula I wherein $R_5$ is

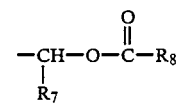

can be obtained by treating the product of formula I wherein $R_5$ is hydrogen with a molar equivalent of a compound of the formula

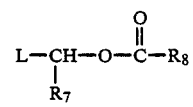

wherein L is a leaving group such as chlorine, bromine, toluenesulfonyloxy, etc., in the presence of base.

The diester products wherein $R_3$ and $R_5$ are the same and are

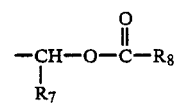

can be obtained by treating the product of formula I wherein $R_3$ and $R_5$ are both hydrogen or an alkali metal salt ion with two or more equivalents of the reagent of formula XV.

The ester products of formula I wherein $R_3$ is

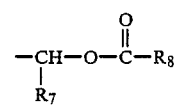

can be obtained by treating the product of formula I wherein $R_3$ is hydrogen or an alkali metal salt and $R_5$ is benzyl or benzhydryl with the compound of formula XV in the presence of base. Removal of the $R_5$ ester group such as by hydrogenation yields the products of formula I wherein $R_3$ is

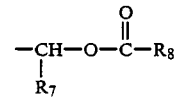

and $R_5$ is hydrogen.

Preferred compounds of this invention are those of formula I wherein $R_1$ is straight or branched chain alkyl of 1 to 4 carbons, or

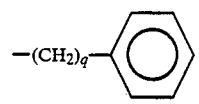

wherein q is an integer from 1 to 4.

$R_2$ is straight or branched chain alkyl of 1 to 4 carbons, trifluoromethyl, or

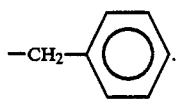

X is NH—(CH$_2$)$_2$—COOR$_5$, COOR$_5$,

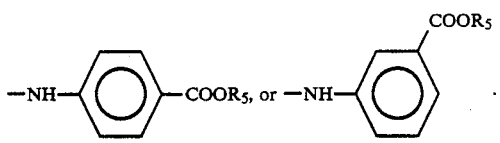

$R_3$ and $R_5$ are hydrogen, straight or branched chain alkyl of 1 to 4 carbons, or an alkali metal salt ion.

The compounds of formula I wherein at least one of $R_3$ and $R_5$ is hydrogen form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

As shown above, the compounds of formula I wherein $R_2$ and $R_4$ are other than hydrogen contain asymmetric centers as represented by the * in formula I. An additional asymmetric center is present in the ester products when $R_7$ is other than hydrogen. Thus, the compounds of formula I can exist in diastereomeric forms or in mixtures thereof. The above described processes can utilize racemates, enantiomers or diastereomers as starting materials. When diastereomeric products are prepared, they can be separated by conventional chromatographic or fractional crystallization methods.

Human as well as other mammalian atria contain specific granules which have been found to contain a precursor to a family of peptides collectively called atrial natriuretic factor (deBold, Science, Vol. 230, p. 767–770, 1985). The biologically active segments of this precursor which circulate in the blood are 21–28 amino acid peptides called atrial natriuretic peptides. These peptides cause diuresis, natriuresis, and relaxation of smooth muscle in blood vessels and other tissues (Needleman et al., Hypertension, Vol. 7, p. 469–482, 1985). The putative circulating hormone in man is a 28 amino acid peptide called human ANF 99–126. Exogenous administration of this peptide to man has been reported to cause diuresis, natriuresis, and a fall in blood pressure (Richards et al., Hypertension, Vol. 7, p. 812–817, 1985).

The compounds of formula I inhibit the activity of neutral endopeptidase (EC 3.4.24.11), a membrane bound zinc metallopeptidase found in many tissues including the brain and kidney. Neutral endopeptidase hydrolyzes peptide bonds which are on the amino terminal side of hydrophobic amino acid residues. Atrial natriuretic peptides have been shown to be cleaved at the Cys$^{105}$-Phe$^{106}$ bond by the action of neutral endopeptidase (Delaney et al., Fed.Proc. 46, p. 1296, 1987; Stephenson et al. Biochem. J., Vol. 243, p. 183–187, 1987). Cleavage of rat ANF 103–126 at Cys$^{105}$-Phe$^{106}$ results in diminishing of its vasorelaxant (Bergey et al. Fed.Proc. 46, p. 1296, 1987) and natriuretic, diuretic and depressor activities (Seymour et al., Fed.Proc.46, p. 1296, 1987). Stephensen et al. reported that the hydrolysis of human ANF 99–126 by pig kidney microvillar membranes in vitro was suppressed by the neutral endopeptidase inhibitor, phosphoramidon.

While not limiting the scope of this invention to a specific theory of mechanism of action, inhibition of neutral endopeptidase is believed to result in reduced inactivation of exogenously administered or endogenous atrial natriuretic peptides. Thus the compounds of formula I are useful in the treatment of hypertension, congestive heart failure, renal failure or hepatic cirrhosis. Diuresis, natriuresis, and blood pressure reduction are produced in a mammalian host such as man by the administration of from about 1 mg. to about 100 mg. per kg. of body weight per day, preferably from about 1 mg. to about 50 mg. per kg. of body weight per day, of one or more neutral endopeptidase inhibitors of formula I or a pharmaceutically acceptable salt thereof. The neutral endopeptidase inhibitors of formula I are preferably administered orally, but parenteral routes such as subcutaneous, intramuscular, and intravenous can also be employed. The daily dose can be administered singly or can be divided into two to four doses administered throughout the day.

The neutral endopeptidase inhibitors of formula I can also be administered in combination with other blood pressure lowering agents. For example, the neutral endopeptidase inhibitors of formula I can be combined for dual administration with an angiotensin converting enzyme (ACE) inhibitor such as captopril, zofenopril, fosinopril, enalapril, lisinopril, etc. Such combination would be at a weight ratio of endopeptidase inhibitor to ACE inhibitor of from about 1:10 to about 10:1.

The neutral endopeptidase inhibitors of formula I can also be administered in combination with human ANF 99–126. Such combination would contain the inhibitor of formula I at from about 1 to about 100 mg. per kg. of body weight and the human ANF 99–126 at from about 0.001 to about 0.1 mg. per kg. of body weight.

The neutral endopeptidase inhibitors of formula I or pharmaceutically acceptable salts thereof can also be administered to a mammalian host such as man to inhibit the degradation of endogenous opioid pentapeptides, [Met$^5$]-enkephalin (Tyr-Gly-Gly-Phe-Met) and [Leu$^5$]-enkephalin (Tyr-Gly-Gly-Phe-Leu), in the brain or in peripheral tissues. Due to its role in the degradation of enkephalinase, brain endopeptidase has often been referred to as "enkephalinase." Enkephalins are neurotransmitters which decrease the perception of pain (Hughes, et al., Nature, Vol. 258, December 1975, p. 577–579). These endogenous opioid peptides are functionally inactivated by cleavage of their Gly$^3$-Phe$^4$ peptide bonds by neutral endopeptidase located at nerve terminals in the brain where enkephalins are released (Malfroy, et al., Nature, Vol. 276, November 1978, p. 523–526). Neutral endopeptidase inhibitors enhance the recovery of endogenous enkephalins released from isolated brain slices (Patey, et al., Science, Vol. 212, June 1981, p. 1153–1155) and cause analgesia in mice that is reversed by the opiate antagonist naloxone (Roques, et al., Nature, Vol. 288, November 1980, p. 286–288). Inhibitors of neutral endopeptidase also show naloxone reversible antidiarrheal effects in rats (Marcais - Collado, et al., European Journal of Pharmacology, Vol. 144, p. 125–132, 1987).

Thus, the compounds of formula I or a pharmaceutically acceptable salt thereof can be administered as an analgesic or antidiarrheal agent to patients orally or parenterally in an effective amount within the daily dosage range of from about 0.1 to about 25 mg. of compound per kg. of patient body weight. Administration can be once daily or in 2 to 4 divided daily doses.

The inhibitors of formula I and other pharmaceutically acceptable ingredients can be formulated for the above described pharmaceutical uses. Suitable compositions for oral administration include tablets, capsules, and elixirs, and suitable compositions for parenteral administration include sterile solutions and suspensions. About 10 to 500 mg. of active ingredient is compounded with physiologically acceptable vehicle, carrier, excipient, binder, preservative, stabilizer, flavoring, etc., in a unit dose form as called for by accepted pharmaceutical practice.

The following examples are illustrative of the invention. Temperatures are given in degrees centigrade.

EXAMPLE 1

3-[[(S)-2-[(Hydroxymethylphosphinyl)oxy]-1-oxo-3phenylpropyl]amino]propanoic acid, dilithium salt (a) (S)-2-Hydroxy-3-phenylpropanoic acid A solution of sodium nitrite (51.8 g., 720 mmole) in water (200 ml.) is added dropwise over 6 hours to a stirred solution of L-phenylalanine (33.04 g., 200 mmole) in 10% sulfuric acid (500 ml.) at 50°. After the addition is complete, the reaction mixture is stirred for 3 hours at 50°, then at room temperature overnight. The reaction mixture is extracted with ethyl acetate (3×200 ml., 2×100 ml.). The combined organic extract is washed with water and brine, dried (Na$_2$SO$_4$), and evaporated to give 28.98 g. of yellow solid. Recrystallization from benzene gives 22.15 g. of (S)-2-hydroxy-3-phenylpropanoic acid as white needles; m.p. 120°–124°; $[\alpha]_D = -29.0°$ (c=1.05, acetone). TLC (silica gel; benzene:acetic acid, 7:3) $R_f$=0.32.

(b) 3-[[(S)-2-Hydroxy-1-oxo-3-phenylpropyl]amino]-propanoic acid, phenylmethyl ester Diisopropylethylamine (7.0 ml., 40 mmole) is added to a suspension of β-alanine, phenylmethyl ester, p-toluenesulfonate (14.05 g., 40 mmole) in dry tetrahydrofuran (120 ml.) at 0° under argon followed by (S)-2-hydroxy-3-phenylpropanoic acid (6.65 g., 40 mmole) and 1-hydroxybenzotriazole hydrate (5.4 g., 40 mmole). A suspension of dicyclohexylcarbodiimide (8.25 g., 40 mmole) in tetrahydrofuran (50 ml.) is added and the reaction mixture is allowed to stir overnight, gradually warming to room temperature. The dicyclohexylurea is filtered and washed with ethyl acetate. The filtrate is evaporated and the residue is taken up in ethyl acetate (300 ml.) and washed with 10% potassium bisulfate, water, 5% sodium bicarbonate, water, and brine, dried (Na$_2$SO$_4$), and evaporated to give 12.18 g. of an oil. Flash chromatography on Merck 9385 silica gel (600 g.) eluting with hexane:ethyl acetate (1:1) gives 8.93 g. of 3-[[(S)-2-hydroxy-1-oxo-3-phenylpropyl]amino]-propanoic acid, phenylmethyl ester as a colorless solid; m.p. 34°–38° . TLC (silica gel; ethyl acetate:hexane, 2:1) $R_f$=0.23.

Anal. calc'd. for C$_{19}$H$_{21}$NO$_4$: C, 69.71; H, 6.46; N, 4.28 Found: C, 69.73; H, 6.46; N, 4.04.

(c) Dibenzyl methylphosphonate

Dibenzylphosphite (5.24 g., 20 mmole) is added in one portion to a suspension of sodium hydride 60% mineral oil dispersion (832 mg., 20.8 mmole) in dimethylformamide (30 ml.) under argon. The resulting mixture is stirred at room temperature for one hour, then at 40° for 30 minutes. The clear amber solution is allowed to cool to room temperature, then a solution of iodomethane (3.36 g., 23.7 mmole) in dimethylformamide (3 ml.) is added over 5 minutes. After an hour of stirring at room temperature, the reaction mixture is poured into 5% potassium bisulfate (200 ml.) and extracted with ethyl acetate (1×100 ml., 4×50 ml.). The combined ethyl acetate extract is washed with 5% sodium bicarbonate (2×50 ml.) and brine, then dried and evaporated to give 4.39 g. of a dark yellow liquid. Flash chromatography on Whatman LPS-1 silica gel (325 g.) eluting with ethyl acetate:hexane (3:2) yields 2.27 g. of dibenzyl methylphosphonate as a slightly yellow liquid. TLC (silica gel; ethyl acetate:hexane, 3:2) $R_f$=0.17.

(d) 3-[[(S)-2-[[(Phenylmethoxy)methylphosphinyl]oxy]-1-oxo-3-phenylpropyl]amino]propanoic acid, phenylmethyl ester Phosphorus pentachloride (1.31 g., 6.3 mmole) is added to a solution of dibenzyl methylphosphonate (1.66 g., 6 mmole) in dry benzene (15 ml.) under nitrogen. The mixture is stirred for 30 minutes at room temperature, then at 60° for 45 minutes. The solvent is evaporated. The residue is taken up in benzene and the resulting solution is evaporated. This sequence is repeated once more to remove the remaining traces of phosphoryl chloride.

A solution of 3-[[(S)-2-hydroxy-1-oxo-3phenylpropyl]amino]propanoic acid, phenylmethyl ester (1.96 g., 6 mmole) and 4-pyrrolidinopyridine (89 mg., 0.6 mmole) in methylene chloride (6 ml.) is added to a solution of the above crude phosphonochloridate in dry methylene chloride (6 ml.) under argon. The mixture is cooled to 0°–5° and a solution of diisopropylethylamine (1.10 ml., 6.3 mmole) in methylene chloride (6 ml.) is added dropwise over 20 minutes. The reaction mixture is stirred for one hour at 0°–5°, then at room temperature overnight. The solvent is evaporated and the residue is taken up in ethyl acetate (175 ml.). This solution is washed with 10% potassium bisulfate, water, 5% sodium bicarbonate, water, and brine, then dried (Na$_2$SO$_4$), and evaporated to give 3.2 g. of a yellow oil. Flash chromatography on Whatman LPS-1 silica gel (300 g.) eluting with ethyl acetate: hexane (6:1) gives 270 mg. of phosphorus ester isomer A with a faster moving impurity, 311 mg. of a mixture of isomers A and B, also contaminated with the fast moving impurity, and 788 mg. of isomer B. The first two fractions are recombined and flash chromatographed on Merck 9385 silica gel eluting with ether-acetone (82:18) to give 180 mg. of 3-[[(S)-2-[[(phenylmethoxy)methylphosphinyl]oxy]-1-oxo-3-phenylpropyl]amino]propanoic acid, phenylmethyl ester (isomer A); m.p. 59°–62°; TLC (silica gel; ether:acetone, 4:1) $R_f$=0.21; 86 mg. of (isomer B); m.p. 74°–77°; TLC (silica gel; ether:acetone, 4:1) $R_f$=0.15; and 236 mg. of mixed isomers. A mixture of these isomers is used in the next step.

(e)
3-[[(S)-2-[(Hydroxymethylphosphinyl)oxy]-1-oxo-3-phenylpropyl]amino]propanoic acid, dilithium salt A solution of the ester product from part (d) (1.07 g., 2.16 mmole) in ethyl acetate (25 ml.) and acetic acid (2.5 ml.) is stirred with 10% palladium on charcoal catalyst (200 mg.) under a flow of hydrogen for 3.5 hours. The catalyst is filtered and the solvent is evaporated. The residue is dissolved in toluene and this solution is evaporated, this procedure is repeated once more. The residue is then suspended in water and treated with 2N lithium hydroxide (2 ml.). The resulting solution is concentrated and applied to a column of HP-20 (porous cross linked polystyrene-divinyl benzene polymer resin, 21×3 cm.) and eluted with water. Product containing fractions are pooled, filtered, and concentrated and then lyophilized to give 0.63 g. of 3-[[(S)-2-[(hydroxymethylphosphinyl)oxy]-1-oxo-3-phenylpropyl]amino]propanoic acid, dilithium salt as a white solid; m.p. greater than 260° (decomposes greater than 249°); $[\alpha]_D = -39.9$ (c=0.98, methanol). TLC (silica gel; chloroform:methanol:acetic acid, 6:1:1) $R_f=0.23$.

Anal. calc'd. for $C_{13}H_{16}NO_6P.2Li.1.75\ H_2O$: C, 43.54; H, 5.48; N, 3.90; P, 8.64 Found: C, 43.54; H, 5.47; N, 3.91; P, 8.40.

EXAMPLE 2

3-[[(S)-2-[[Hydroxy(2-phenylethyl)phosphinyl]oxy]1-oxo-3-phenylpropyl]amino]propanoic acid, dilithium salt (a) Dibenzyl phenethylphosphonate Dibenzylphosphite (11.93 ml., 54 mmole) is added dropwise to a stirred suspension of prewashed sodium hydride (1.45 g., 59.4 mmole) in dry dimethylformamide (40 ml.) under argon at room temperature. After 1.5 hours at room temperature, the brown homogeneous mixture is treated with phenethyl bromide (7.38 ml., 54 mmole) and then stirred for 20 minutes. The mixture is then partitioned between 5% potassium bisulfate and ethyl acetate, the organic layer is washed with brine, dried ($Na_2SO_4$), and evaporated to a viscous yellow oil (20.6 g.). This crude oil is flash chromatographed on Whatman LPS-1 silica gel eluting with hexane:ethyl acetate (7:3). Product fractions are evaporated to give 12.6 g. of dibenzyl phenethylphosphonate as a clear, colorless oil. TLC (silica gel; petroleum ether:ether, 1:1) $R_f=0.11$.

(b)
3-[[(S)-2-[[Phenylmethoxy(2-phenylethyl)phosphinyl]oxy]-1-oxo-3-phenylpropyl]amino]propanoic acid, phenylmethyl ester A solution of dibenzyl phenethylphosphonate (2.20 g., 6 mmole) in dry benzene (15 ml.) is treated with phosphorus pentachloride (1.3 g., 6.3 mmole) and the reaction mixture is stirred at ambient temperature under nitrogen for 30 minutes, then at 60° for 45 minutes. The solvent is evaporated in vacuo, and the residue is dissolved in dry benzene and again evaporated in vacuo (twice).

The above crude phosphonochloridate is dissolved in freshly distilled methylene chloride (6 ml.) and treated with a solution of 3-[[(S)-2-hydroxy-1-oxo-3-phenylpropyl]amino]propanoic acid, phenylmethyl ester (1.96 g., 6 mmole) and 4-pyrrolidinopyridine (89 mg., 0.6 mmole) in freshly distilled methylene chloride (6 ml.). The reaction mixture is cooled in an ice bath under nitrogen and treated dropwise with a solution of diisopropylethylamine (814 mg., 6.3 mmole) in freshly distilled methylene chloride (6 ml.) over 20 minutes. The reaction mixture is stirred in the cold for one hour, then at ambient temperature overnight. The solvent is evaporated in vacuo. The residue is taken up in ethyl acetate (175 ml.) and washed with 40 ml. portions of 10% aqueous potassium bisulfate, water, 5% aqueous sodium bicarbonate, water, and brine, then dried ($MgSO_4$), and concentrated in vacuo to yield 3.7 g. of crude product. Flash chromatography on Merck 9385 silica gel (300 g., 230–400 mesh) eluting with hexane:ethyl acetate (1:2) gives 840 mg. of 3-[[(S)-2-[[phenylmethoxy(2-phenylethyl)phosphinyl]oxy]-1-oxo-3-phenylpropyl]amino]propanoic acid, phenylmethyl ester as an oil. TLC (silica gel; hexane:ethyl acetate, 1:2) $R_f=0.35$ (minor impurity at 0.42).

(c)
3-[[(S)-2-[[Hydroxy(2-phenylethyl)phosphinyl]oxy]-1-oxo-3-phenylpropyl]amino]propanoic acid, dilithium salt A solution of the ester product from part (b) (840 mg., 1.7 mmole) in ethyl acetate (25 ml.) and acetic acid (2.5 ml.) is treated with 10% palladium on carbon catalyst (225 mg.) and subjected to a slow flow of hydrogen at 1 atmosphere pressure. After 3 hours, the reaction is filtered through a microcrystalline cellulose pad, concentrated in vacuo, azeotroped with toluene and methylene chloride, and concentrated in vacuo to give 520 mg. of crude free acid.

This free acid is dissolved in aqueous methanol and treated with 2N lithium hydroxide (1.2 ml.). The solution is filtered (Millipore) and concentrated in vacuo. The residue is dissolved in a minimal volume of water and chromatographed on an HP-20 column (150 ml.) eluting with a gradient from 500 ml. of water to 500 ml. of acetonitrile. The product containing fractions are pooled, concentrated, and lyophilized from water to give 460 mg. of crude dilithium salt. The entire amount is reapplied to the exact same column and eluted under identical conditions to give 413 mg. of partially purified product. This is combined with 510 mg. of a dilithium salt of similar purity prepared in another run and the combined product (923 mg.) is rechromatographed on an HP-20 column (150 ml.) in two batches and eluted with a gradient from 500 ml. of water to 500 ml. of acetonitrile. The product containing fractions are pooled, concentrated in vacuo, and lyophilized from water to give 750 mg. of 3-[[(S)-2-[[hydroxy(2-phenylethyl)phosphinyl]oxy]-1-oxo-3-phenylpropyl]amino]propanoic acid, dilithium salt as a white solid; m.p. 195° to greater than 250°; $[\alpha]_D = -35.3°$ (c=1, methanol). TLC (silica gel; chloroform:methanol:acetic acid, 4:1:1) $R_f=0.56$.

Anal. calc'd. for $C_{20}H_{22}NO_6P.2Li.1.7H_2O$: C, 53.52; H, 5.72; N, 3.12; P, 6.9. Found: C, 53.49; H, 5.44; N, 3.11; P, 6.8.

EXAMPLE 3

3-[[(S)-2-[[Hydroxy(phenylmethyl)phosphinyl]oxy]-1-oxo-3-phenylpropyl]amino]propanoic acid, dilithium salt (a) Dimethoxy phenylmethylphosphonate Trimethyl phosphite (43.43 g., 350 mmole) is heated to 90° under a flow of nitrogen and treated dropwise with benzyl bromide (17.10 g., 100 mmole). Once the addition is completed, the reaction is heated at reflux under a flow of nitrogen overnight. Unreacted trimethyl phosphite and dimethyl methylphosphonate are removed via distillation in vacuo (pot temperature 120°, 10 mm. of Hg.) to give 29.8 g. of crude reaction product as the residue. Flash chromatography on Merck 9385 silica gel (300 g.) eluting with 3:1 petroleum ether:acetone affords 5.5 g. of dimethoxy phenylmethylphosphonate as a colorless oil. TLC (silica gel; petroleum ether: acetone, 1:1) $R_f$=0.48.

(b) 3-[[(S)-2-[[Methoxy(phenylmethyl)phosphinyl]oxy]-1-oxo-3-phenylpropyl]amino]propanoic acid, phenylmethyl ester A solution of dimethoxy phenylmethylphosphonate (1.20 g., 6 mmole) in dry benzene (15 ml.) under nitrogen is treated with phosphorus pentachloride (1.3 g., 6.3 mmole). The mixture is stirred at room temperature for 30 minutes and then at 60° for 45 minutes. The solvent is removed in vacuo. The residue is dissolved in dry benzene and this solution is concentrated in vacuo to give the phosphonochloridate.

A solution of the above phosphonochloridate in dry methylene chloride (6 ml.) is treated with a solution of 3-[[(S)-2-hydroxy-1-oxo-3-phenylpropyl]amino]-propanoic acid, phenylmethyl ester (1.96 g., 6 mmole) and 4-pyrrolidinopyridine (89 mg., 0.6 mmole) in methylene chloride (6 ml.). The reaction mixture is cooled in an ice bath under nitrogen and treated dropwise with a solution of diisopropylethylamine (814 mg., 6.3 mmole) in dry methylene chloride (6 ml.). The reaction mixture is stirred in the cold for one hour and then at room temperature overnight. The mixture is concentrated in vacuo. The residue is dissolved in ethyl acetate (175 ml.) and washed successively with 40 ml. portions of 10% potassium bisulfate, water, 5% sodium bicarbonate, water, and brine, dried (MgSO$_4$), and concentrated in vacuo to give 3.9 g. of crude product. Purification by flash chromatography on Merck 9385 silica gel (390 g.) eluting with ethyl acetate:hexanes (2:1) followed by 1% methanol in ethyl acetate gives 1.73 g. of 3-[[(S)-2-[[methoxy(phenylmethyl)phosphinyl]oxy]-1-oxo-3-phenylpropyl]amino]propanoic acid, phenylmethyl ester. TLC (silica gel; 1% methanol in ethyl acetate) $R_f$=0.46 (minor impurities at 0.62 and 0.74).

(c) 3-[[(S)-2-[[Methoxy(phenylmethyl)phosphinyl]oxy]-1-oxo-3-phenylpropyl]amino]propanoic acid A solution of the propanoic acid, phenylmethyl ester product from part (b) (1.7 g., 3.43 mmole) in ethyl acetate (50 ml.) and acetic acid (5 ml.) is treated with 10% palladium on carbon catalyst (500 mg.) and the resulting mixture is stirred at room temperature and subjected to a steady stream of hydrogen at one atmosphere pressure. After 2 hours, the catalyst is removed by filtration through a cellulose microfilter and the filtrate is concentrated in vacuo to yield 1.45 g. of crude product. Flash chromatography on Merck 9385 silica gel (140 g.) eluting with methylene chloride: methanol:acetic acid (30:1:1) yields 1.28 g. of 3-[[(S)-2-[[methoxy(phenylmethyl)phosphinyl]oxy]-1-oxo-3-phenylpropyl]amino]propanoic acid as an oil. TLC (silica gel; chloroform:methanol:acetic acid, 30:1:1) $R_f$=0.23 (minor impurity at $R_f$=0.32).

Anal. calc'd for $C_{20}H_{24}NO_6P \cdot 0.4H_2O$: C, 58.14; H, 6.07; N, 3.39; P, 7.50 Found: C, 58.14; H, 6.07; N, 3.10; P, 7.1.

(d) 3-[[(S)-2-[[Hydroxy(phenylmethyl)phosphinyl]oxy]-1-oxo-3-phenylpropyl]amino]propanoic acid, dilithium salt A solution of the product from part (c) (1.0 g., 2.47 mmole) in acetone (10 ml.) is saturated with trimethylamine gas and heated in a sealed tube at 80° overnight. The excess trimethylamine is removed by attachment to a water aspirator. The reaction is concentrated in vacuo and the residue is partitioned between 100 ml. each of ethyl acetate and 0.1N hydrochloric acid. The organic layer is separated, washed with brine, dried (MgSO$_4$), and concentrated to give 460 mg. of crude product. Additional product is recovered by salting out the aqueous layer and extracting with ethyl acetate (3×25 ml.). The combined organic extracts are dried (MgSO$_4$) and concentrated to yield an additional 200 mg. of crude product. An additional 170 mg. of crude product prepared by an identical procedure is combined with the above material and chromatographed on a column of HP-20 resin (2.5×20 cm.) eluting with a gradient from 500 ml. of water to 500 ml. of acetonitrile to yield 720 mg. of partially purified product. This material is divided into two batches. Each batch is dissolved in methanol, water is added until the compound just stays in solution, and the resulting solution is treated with 2N lithium hydroxide (1.84 ml., 3.86 mmole). The lithium salts are chromatographed separately on the same HP-20 column, again eluting with a gradient from 500 ml. of water to 500 ml. of acetonitrile. The product obtained from each chromatography is combined, dissolved in water, filtered through a microfilter and lyophilized to give 623 mg. of 3-[[(S)-2-[[hydroxy(phenylmethyl)phosphinyl]oxy]-1-oxo-3-phenylpropyl]amino]propanoic acid, dilithium salt as a white solid; m.p. 198° to greater than 250°; $[\alpha]_D$= −31.0° (c=0.5, methanol). TLC (silica gel; chloroform:methanol:acetic acid, 6:1:1) $R_f$=0.35 (minor impurity at 0.20).

Anal calc'd. for $C_{19}H_{20}NO_6P \cdot 2Li \cdot 1.8H_2O$: C, 52.43; H, 5.46; N, 3.22; P, 7.12 Found: C, 52.43; H, 5.32; N, 3.26; P, 7.1.

EXAMPLE 4

3-[[(S)-2-[[Hydroxy(4-phenylbutyl)phosphinyl]oxy]-1-oxo-3-phenylpropyl]amino]propanoic acid (a) (4-Phenylbutyl)phosphinic acid To a suspension of sodium hypophosphite hydrate (60 g., 0.566 mole) in absolute ethanol (600 ml.) is added concentrated sulfuric acid (15 ml.), 4-phenyl-1-butene (25.0 g., 0.189 mole) and 2,2'-azobisisobutyronitrile (3.0 g.). The resulting mixture is refluxed for 6 hours, treated with a second portion of 2,2'-azobisisobutyronitrile (2.0 g.), and refluxed for an additional 16 hours. The cooled mixture is filtered and concentrated in vacuo. The residue is suspended in water (200 ml.), made basic with 50% sodium hydroxide solution, and washed with two portions of ethyl ether (200 ml. each). The aqueous phase is acidified with concentrated sulfuric acid and extracted with ethyl acetate. The ethyl acetate extract is washed with saturated sodium chloride, dried over anhydrous sodium sulfate, and evaporated to give 34.5 g. of crude (4-phenylbutyl) phosphinic acid.

This crude acid (34.5 g.) is taken up in ethyl ether (200 ml.) and treated with a solution of 1-adamantanamine (26.3 g., 0.174 mole) in ethyl ether (200 ml.). The white precipitate is collected, washed with ethyl ether, and dried in vacuo to give 54.2 g. of (4-phenylbutyl) phosphinic acid, 1-adamantanamine salt as a white solid; m.p. 192°-200°.

This 1-adamantanamine salt (2.72 g., 7.8 mmole) is partitioned between ethyl acetate (75 ml.) and 1N hydrochloric acid (50 ml.). The ethyl acetate layer is washed with 1N hydrochloric acid and saturated sodium chloride, dried over anhydrous sodium sulfate and evaporated to give 1.46 g. of (4-phenylbutyl)phosphinic acid as a slightly yellow oil.

(b)
3-[[(S)-2-[[(4-Phenylbutyl)phosphinyl]oxy]-1-oxo-3-phenylpropyl]amino]propanoic acid phenylmethyl ester A solution of (4-phenylbutyl)phosphinic acid (1.46 g., 7.37 mmole) and 3-[[(S)-2-hydroxy-1-oxo-3-phenylpropyl]amino]propanoic acid, phenylmethyl ester (1.96 g., 6 mmole) in dry tetrahydrofuran (25 ml.) is treated with dicyclohexylcarbodiimide (1.61 g., 7.8 mmole) and dimethylaminopyridine (73 mg., 0.6 mmole). The mixture is stirred at room temperature under argon for 80 minutes and then filtered. The filtrate is concentrated in vacuo and the residue is taken up in ethyl acetate (150 ml.). This solution is washed successively with 5% potassium bisulfate, 5% sodium bicarbonate, water, and saturated sodium chloride solution, dried ($Na_2SO_4$), and evaporated to yield 3.30 g. of 3-[[(S)-2-[[(4-phenylbutyl)phosphinyl]oxy]-1-oxo-3-phenylpropyl]amino]propanoic acid, phenylmethyl ester as a white solid, m.p., 59°-68°. TLC (silica gel; ethyl acetate) $R_f=0.23$ (traces at 0.38, 0.43 and 0.48).

Anal. calc'd. for $C_{29}H_{34}NO_5P.0.38 H_2O$: C, 67.71; H, 6.81; N, 2.72; P, 6.02 Found: C, 67.70; H, 6.82; N, 2.98; P, 5.8.

(c)
3-[[(S)-2-[[Hydroxy(4-phenylbutyl)phosphinyl]oxy]-1-oxo-3-phenylpropyl]amino]propanoic acid, phenylmethyl ester A solution of the phenylmethyl ester product from part (b) (3.10 g., 6.03 mmole) in dioxane (30 ml.) is treated with a solution of sodium periodate (1.39 g., 6.49 mmole) in water (10 ml.) and stirred at room temperature under argon for 15 hours. The mixture is diluted with ethyl acetate and washed successively with water, dilute sodium metabisulfite in 1% potassium bisulfate (until the iodine color is discharged), water, and saturated sodium chloride solution. The organic phase is dried ($Na_2SO_4$) and evaporated. The residue is taken up in hot toluene and this solution is filtered and evaporated to yield 3.21 g. of crude 3-[[(S)-2-[[hydroxy-(4-phenylbutyl)phosphinyl]oxy]-1-oxo-3-phenylpropyl]amino]propanoic acid, phenylmethyl ester as a white solid; m.p. 64°-70°. TLC (silica gel; chloroform:methanol:acetic acid, 23:1:1) $R_f=0.18$ (minor spot at 0.40). This crude product is used in the next step.

(d)
3-[[(S)-2-[[Hydroxy(4-phenylbutyl)phosphinyl]oxy]-1-oxo-3-phenylpropyl]amino]propanoic acid A solution of the phenylmethyl ester product from part (c) (2.5 g., 4.77 mmole) in ethyl acetate (50 ml.) and acetic acid (5 ml.) is stirred with 10% palladium on carbon catalyst (400 mg.) at room temperature under a slow flow of hydrogen for 16 hours. The catalyst is removed by filtration and the filtrate is evaporated to give 1.81 g. of white solid. Recrystallization of this material from hot water and further recrystallizations of the material recovered from the mother liquor affords 1.07 g. of pure diacid. A portion of the crude material (0.58 g.) recovered from the mother liquors is treated with 2N lithium hydroxide (approximately 1.2 ml.). The solution is filtered, concentrated, and applied to a column of HP-20(2.5×20 cm.) packed in water. The column is eluted with a linear gradient of from 400 ml. of water to 400 ml. of acetonitrile. Product containing fractions are pooled and concentrated to give 0.55 g. of dilithium salt. A solution of this salt in water (25 ml.) is acidified to a pH of 2 with concentrated hydrochloric acid and the product that separates is extracted into ethyl acetate. The ethyl acetate extract is washed with water and saturated sodium chloride, dried ($Na_2SO_4$), and evaporated to afford an additional 0.45 g. of pure diacid. The 1.07 g. and 0.45 g. portions are combined to yield 1.52 g. of white solid 3-[[(S)-2-[[hydroxy(4-phenylbutyl)phosphinyl]oxy]-1-oxo-3-phenylpropyl]amino]propanoic acid: m.p. 78.5°-80°: $[\alpha]_D=-20.0°$ (c=1, methanol). TLC (silica gel; isopropanol:water:ammonia, 8:2:1) $R_f=0.59$ with heading (trace at origin). TLC (silica gel; chloroform:methanol:acetic acid, 6:1:1) $R_f=0.39$ (trace at 0.06).

Anal. calc'd. for $C_{22}H_{28}NO_6P$: C, 60.96; H, 6.51; N, 3.23; P, 7.15 Found: C, 60.75; H, 6.56; N, 3.22; P, 7.0.

EXAMPLE 5

3-[[(S)-2-[[Hydroxy(3-phenylpropyl)phosphinyl]oxy]-1-oxo-3-phenylpropyl]amino]propanoic acid (a) (3-Phenylpropyl)phosphinic acid, 1-adamantanamine salt 2,2'-Azobisisobutyronitrile (3 g.) is added to a stirred mixture of 3-phenyl-1-propene (22.3 g., 188.7 mmole), sodium hypophosphite hydrate (60 g., 566 mmole, 3 eq.) in absolute ethanol (600 ml.), and concentrated sulfuric acid (15 ml.). The white suspension is refluxed for 3 hours, additional 2,2'-azobisisobutyronitrile (2 g.) is added, and the mixture is refluxed for 16 more hours. The cooled mixture is filtered, the solids are rinsed with ethanol and the filtrate is evaporated to an oil. The resulting oil is taken up in water (100 ml.), made basic (pH of approximately 13) by the addition of 50% sodium hydroxide (about 25 ml.), cooled, and then washed with ethyl ether (2×100 ml.). The aqueous layer is acidified with concentrated sulfuric acid (12 ml.) and extracted with ethyl acetate. The ethyl acetate extract is washed with brine, dried over anhydrous sodium sulfate, and evaporated to give 31.55 g. of crude (3-phenylpropyl)phosphinic acid as a clear oil.

This crude acid (18.4 g., 99.4 mmole) is taken up in ethyl ether (30 ml.) and adamantanamine (15.1 g., 100 mmole) in ethyl ether (60 ml.) is added. The precipitate is collected by filtration, rinsed with ethyl ether, and dried in vacuo to give 29.7 g. of (3-phenylpropyl)phosphinic acid, 1-adamantanamine salt as a white, crystalline solid; m.p. 204°-207°. TLC (silica gel; isopropanol:ammonia:water, 7:2:1) $R_f=0.62$.

(b)
3-[[(S)-2-[[(3-Phenylpropyl)phosphinyl]oxy]-1-oxo-3-phenylpropyl]amino]propanoic acid, phenylmethylester (3-Phenylpropyl)phosphinic acid is regenerated from the above adamantanamine salt (2.18 g., 6.5 mmole) by partitioning between ethyl acetate (75 ml.) and 1N hydrochloric acid (50 ml.). The ethyl acetate layer is washed with 1N hydrochloric acid and saturated sodium chloride, dried (Na$_2$SO$_4$), and evaporated to give 1.05 g. of (3-phenylpropyl)phosphinic acid as a slightly yellow oil.

A solution of (3-phenylpropyl)phosphinic acid (1.05 g., 5.7 mmole) and 3-[[(S)-2-hydroxy-1-oxo-3-phenyl-propyl]amino]propanoic acid, phenylmethyl ester (1.64 g., 5 mmole) in dry tetrahydrofuran (21 ml.) is treated with dicyclohexylcarbodiimide (1.18 g., 5.70 mmole) and dimethylaminopyridine (61 mg., 0.5 mmole). The mixture is stirred at room temperature under argon for 45 minutes and then treated with an additional amount of (3-phenylpropyl)phosphinic acid (0.15 g., 0.82 mmole) dissolved in tetrahydrofuran (5 ml.) followed by an additional amount of dicyclohexylcarbodiimide (169 mg., 0.82 mmole). After 30 minutes the mixture is diluted with ether and filtered. The filtrate is evaporated and the residue is taken up in ethyl acetate (50 ml.). This solution is filtered, washed successively with 5% potassium bisulfate, 5% sodium bicarbonate, water, and saturated sodium chloride, dried (Na$_2$SO$_4$), and evaporated to yield 2.64 g. of 3-[[(S)-2-[[(3-phenylpropyl)phosphinyl]oxy]-1-oxo-3-phenylpropyl]amino]propanoic acid, phenylmethyl ester as a nearly colorless oil. TLC (silica gel; chloroform:methanol:acetic acid, 20:1:1) R$_f$=0.53.

(c)
3-[[(S)-2-[[Hydroxy(3-phenylpropyl)phosohinyl]-oxy]-1-oxo-3-phenylpropyl]amino]propanoic acid, phenylmethyl ester A solution of the phenylmethyl ester product from part (b) (2.48 g., 4.70 mmole) in dioxane (25 ml.) is treated with a solution of sodium periodate (1.16 g., 5.4 mmole) in water (10 ml.) and stirred at room temperature under argon for 15 hours. The dark orange suspension is diluted with ethyl acetate (100 ml.) and washed successively with a 2% solution of sodium metabisulfite in 5% potassium bisulfate (until the orange color is discharged), water and saturated sodium chloride solution. The organic phase is dried over sodium sulfate and evaporated to give 2.6 g. of a slightly yellow viscous oil. This crude product is purified by formation of a salt with 1-adamantanamine (722 mg., 4.78 mmole) in ether.

The white solid (2.76 g.) that separates after the addition of hexane and trituration is collected and then recrystallized from ethyl acetate-hexane to give 2.57 g. of the adamantanamine salt. The free acid is regenerated by partitioning this salt between ethyl acetate (75 ml.) and 1N hydrochloric acid (50 ml.). The organic phase is washed with 1N hydrochloric acid, water, and saturated sodium chloride, then dried over sodium sulfate, and evaporated to yield 2.06 g. of 3-[[(S)-2-[[hydroxy(3-phenylpropyl)phosphinyl]oxy]-1-oxo-3-phenylpropyl]amino]propanoic acid, phenylmethyl ester as a colorless oil. TLC(silica gel; chloroform:methanol:acetic acid, 20:1:1) R$_f$=0.25 (trace at origin).

Anal. calc'd for C$_{28}$H$_{32}$NO$_6$P: C, 66.00; H, 6.33; N, 2.75; P, 6.08 Found: C, 65.67; H, 6.34; N, 2.60; P, 6.0.

(d)
3-[[(S)-2-[[Hydroxy(3-phenylpropyl)phosphinyl]oxy]-1-oxo-3-phenylpropyl]amino]propanoic acid A solution of the phenylmethyl ester product from part (c) (1.95 g., 3.82 mmole) in ethyl acetate (40 ml.) and acetic acid (4 ml.) is stirred with 10% palladium on carbon catalyst (320 mg.) at room temperature under a slow flow of hydrogen for 18 hours. The catalyst is removed by filtration and the filtrate is evaporated. The residue is taken up in ethyl acetate and the resulting solution is concentrated. This procedure is repeated twice to give 1.5 g. of colorless gum. Trituration with water gives 1.32 g. of powdery white solid 3-[[(S)-2-[[hydroxy(3-phenylpropyl)phosphinyl]oxy]-1-oxo-3-phenylpropyl]amino]propanoic acid; m.p. 74°–79.5° (loss of solvent 60°–65°); [α]$_D$=−17.7° (c=1, methanol). TLC (silica gel; isopropanol:water:ammonia, 8:2:1) R$_f$=0.54 with heading (trace at origin). TLC (silica gel; chloroform:methanol:acetic acid, 6:1:1) R$_f$=0.37 (trace at 0.06).

Anal. calc'd for C$_{21}$H$_{26}$NO$_6$P·0.66 H$_2$O: C, 58.48; H, 6.38; N, 3.25; P, 7.18 Found: C, 58.48; H, 6.48; N, 3.23; P, 6.9.

EXAMPLE 6

3-[[(S)-2-[[Hydroxy(2-phenylethyl)phosphinyl]amino]-1-oxo-3-phenylpropyl]amino]propanoic acid, dilithium salt (a)
3-[[(S)-2-[[(1,1-Dimethylethoxy)carbonyl]amino]-1-oxo-3-phenylpropyl]amino]propanoic acid, phenylmethyl ester A suspension of β-alanine, phenylmethyl ester, p-toluenesulfonate (14.05 g., 40 mmole) in dry tetrahydrofuran (120 ml.) is treated with diisopropylethylamine (5.2 g., 40 mmole), followed by N-[(1,1-dimethylethoxy)carbonyl]-L-phenylalanine (10.61 g., 40 mmole) and 1-hydroxybenzotriazole hydrate (5.4 g., 40 mmole). The resulting solution is cooled in an ice bath and treated with dicyclohexylcarbodiimide (8.25 g., 40 mmole). The reaction mixture is allowed to stir for one hour in the cold, then at ambient temperature for 40 hours. The reaction mixture is diluted with ether (35 ml.), filtered to remove dicyclohexylurea, and then concentrated in vacuo. The residue is taken up in ethyl acetate (300 ml.). The resulting solution is filtered, washed successively with 10% potassium bisulfate, 5% sodium bicarbonate, and brine (3×50 ml. each), dried (Na$_2$SO$_4$), and concentrated in vacuo to give 16.8 g. of a white solid. Recrystallization from ethyl acetate-hexane gives 13.84 g. of 3-[[(S)-2-[[(1,1-dimethylethoxy)carbonyl]amino]-1-oxo-3-phenylpropyl]amino]propanoic acid, phenylmethyl ester as white needles; m.p. 93°–96°. TLC (silica gel; ethyl acetate:hexane, 1:1) R$_f$=0.32.

Anal. calc'd for C$_{24}$H$_{30}$N$_2$O$_5$: C, 67.59; H, 7.09; N, 6.57 Found: C, 67.51; H, 7.14; N, 6.66.

(b)
3-[[(S)-2-Amino-1-oxo-3-phenylpropyl]amino]-propanoic acid, phenylmethyl ester, hydrochloride A solution of the phenylmethyl ester product from part (a) (13.65 g., 32 mmole) in 1.5N hydrogen chloride gas in acetic acid solution (90 ml.) is stirred for 90 minutes at room temperature, and then the solvent is evaporated in vacuo. The residue is triturated in ether and the resulting white precipitate is collected to give 11.45 g.

of crude product as a powdery white solid; m.p. 169°-175°. TLC (silica gel; chloroform:methanol:acetic acid, 6:1:1) $R_f=0.52$. One recrystallization from acetonitrile gives an analytical sample of 3-[[(S)-2-amino-1-oxo-3-phenylpropyl]amino]propanoic acid, phenylmethyl ester, hydrochloride as white needles; m.p. 170.5°-175°.

Anal. calc'd. for $C_{19}H_{23}N_2O_3Cl$: C, 62.89; H, 6.39; N, 7.72; Cl, 9.77 Found: C, 62.78; H, 6.46; N, 7.71; Cl, 9.60.

(c) Dimethyl phenethylphosphonate

A mixture of phenethyl bromide (18.5 g., 100 mmole) and freshly distilled trimethylphosphite (43.4 g., 350 mmole) is heated at reflux under nitrogen overnight. The unreacted trimethylphosphite is distilled off in vacuo and the remaining mixture is distilled at a pressure of 5 mm. of Hg. and a bath temperature of 105°, leaving a residue of 23.7 g. of crude product. Flash chromatography on Merck 9385 silica gel (237 g.) eluting with petroleum ether:acetone (5:1) gives 9.9 g. of dimethyl phenethylphosphonate as a colorless liquid. TLC (silica gel; petroleum ether:acetone, 1:1) $R_f=0.45$.

Anal. calc'd. for $C_{10}H_{15}O_3P \cdot 0.5\ H_2O$: C, 53.88; H, 7.22; P, 13.89 Found: C, 53.88; H, 6.84; P, 13.9.

(d)
3-[[(S)-2-[[Methoxy(2-phenylethyl)phosphinyl]amino]-1-oxo-3-phenylpropyl]amino]propanoic acid, phenylmethyl ester The hydrochloride product from part (b) (1.81 g., 5 mmole) is partitioned between ethyl acetate and 5% sodium bicarbonate (200 ml. each). The organic layer is washed with brine, dried (MgSO$_4$), and concentrated in vacuo to yield 3-[[(S)-2-amino-1-oxo-3-phenylpropyl]amino]propanoic acid, phenylmethyl ester.

A solution of dimethyl phenethylphosphonate (1.07 g., 5 mmole) in dry benzene (15 ml.) under nitrogen is treated with phosphorus pentachloride (1.09 g., 5.25 mmole). The mixture is stirred at room temperature for 30 minutes, and then at 60° (bath temperature) for 45 minutes. The solvent is removed in vacuo. The residue is dissolved in dry benzene and this solution is concentrated in vacuo (twice) to give the phosphonochloridate.

A solution of this phosphonochloridate (about 5 mmole) in dry methylene chloride (8 ml.) is cooled in an ice bath under nitrogen and treated with a solution of the above 3-[[(S)-2-amino-1-oxo-3-phenylpropyl]amino]propanoic acid, phenylmethyl ester (about 5 mmole) and 4-pyrrolidinopyridine (74 mg., 0.5 mmole) in methylene chloride (8 ml.). The mixture is treated dropwise with a solution of diisopropylethylamine (646 mg., 5 mmole) in methylene chloride (8 ml.). The reaction mixture is stirred in the cold for one hour, and then at room temperature overnight. The mixture is concentrated in vacuo. The residue is dissolved in ethyl acetate (250 ml.) and this solution is washed successively with 10% potassium bisulfate, water, 5% sodium bicarbonate, water, and brine (50 ml. each), dried (MgSO$_4$), and concentrated in vacuo to give 2.1 g. of a yellow oil. Purification by flash chromatography on Merck 9385 silica gel (137 g.) eluting with petroleum ether:acetone (1:1) gives 1.15 g. of 3-[[(S)-2-[[methoxy(2-phenylethyl)phosphinyl]amino]-1-oxo-3-phenylpropyl]amino]propanoic acid, phenylmethyl ester. TLC (silica gel; petroleum ether:acetone, 1:1) $R_f=0.29$ (minor impurity at 0.50).

Anal. calc'd. for $C_{28}H_{33}N_2O_5P \cdot 0.3\ H_2O$: C, 65.32; H, 6.60; N, 5.44; P, 6.02 Found: C, 65.37; H, 6.84; N, 5.48; P, 5.9.

(e)
3-[[(S)-2-[[Methoxy(2-phenylethyl)phosphinyl]amino]-1-oxo-3-phenylpropyl]amino]propanoic acid A solution of the phenylmethyl ester product from part (d) (1.1 g., 2.2 mmole) in 95% ethanol (50 ml.) is treated with 10% palladium on carbon catalyst (200 mg.) and the resulting mixture is stirred at room temperature and subjected to a steady stream of hydrogen at 1 atmosphere pressure. After 4 hours, the catalyst is removed by filtration through a cellulose microfilter and the filtrate is concentrated in vacuo to give 900 mg. of crude product. Flash chromatography on Merck 9385 silica gel (50 g.) eluting with methylene chloride: methanol:acetic acid (50:1:1) gives 790 mg. of partially purified material. A second flash chromatography on Merck 9385 silica gel (79 g.) eluting with toluene:acetic acid (6:1) gives 610 mg. of 3-[[(S)-2-[[methoxy(2-phenylethyl)phosphinyl]amino]-1-oxo-3-phenylpropyl]amino]propanoic acid. TLC (silica gel; toluene:acetic acid, 6:1) $R_f=0.12$.

Anal. calc'd. for $C_{21}H_{27}N_2O_5P$: C, 60.28; H, 6.50; N, 6.70; P, 7.40 Found: C, 60.47; H, 6.78; N, 6.34; P, 6.8.

(f)
3-[[(S)-2-[[Hydroxy(2-phenylethyl)phosphinyl]amino]-1-oxo-3-phenylpropyl]amino]propanoic acid, dilithium salt A solution of the propanoic acid product from part (e) (580 mg., 1.39 mmole) in dry methylene chloride (7 ml.) under nitrogen is treated with bis(trimethylsilyl)acetamide (366 mg., 1.8 mmole), and then stirred at room temperature for 2 hours. The reaction mixture is concentrated in vacuo. The residue is dissolved in dry methylene chloride (5 ml.) under nitrogen and then treated with bromotrimethylsilane (468 mg., 3.06 mmole). The mixture is stirred at ambient temperature overnight and then treated with a solution of triethylamine (789 mg., 7.8 mmole) in methanol (4.3 ml.) and water (1.08 ml.). After 30 minutes of stirring at ambient temperature, the mixture is concentrated in vacuo. The residue is dissolved in water (approximately 3 ml.) and passed through a 30 ml. column of AG50W-X8 (Li$^+$ form) resin eluting with water. The product containing fractions are pooled and concentrated to give 940 mg. of a white solid. Chromatography on a column of HP-20 (2.5×20 cm.) eluting with a linear gradient from 500 ml. of water to 500 ml. of acetonitrile gives 432 mg. of 3-[[(S)-2-[[hydroxy(2-phenylethyl)phosphinyl]amino]-1-oxo-3-phenylpropyl]amino]propanoic acid, dilithium salt as a white solid; m.p. greater than 250°; $[\alpha]_D = -12.0°$ (c=0.5, methanol). TLC (silica gel; isopropanol:water:ammonia, 8:2:1) $R_f=0.43$ with heading (trace at 0.55).

Anal. calc'd. for $C_{20}H_{23}N_2O_5P \cdot 2Li \cdot 1.7\ H_2O$: C, 53.75; H, 5.95; N, 6.27; P, 6.93 Found: C, 53.79; H, 5.65; N, 6.28; P, 6.9.

EXAMPLE 7

3-[[(S)-2-[[Hydroxy(2-phenylethyl)phosphinyl]amino]-1-oxopropyl]amino]propanoic acid, dilithium salt (a) β-Alanine, methyl ester, hydrochloride A stirred suspension of β-alanine (16 g., 180 mmole) in methanol (400 ml.) is cooled to −10° under nitrogen and treated dropwise with thionyl chloride (42.8 g., 360 mmole) while maintaining the temperature between −5° and −10°. After the addition is complete, the reaction mixture is allowed to warm to ambient temperature overnight. The reaction mixture is concentrated in vacuo, and the residue is twice triturated with ether to give 24.7 of β-alanine, methyl ester, hydrochloride as a solid; m.p. 102°–105°. TLC (silica gel; n-butanol:acetic acid:water, 4:1:1) $R_f$=0.44 with tailing.

(b)
3-[[(S)-2-[[(1,1-Dimethylethoxy)carbonyl]amino]-1-oxopropyl]amino]propanoic acid, methyl ester A solution of β-alanine, methyl ester, hydrochloride (8.38 g., 60 mmole) in dry dimethylformamide (75 ml.) is treated with N-[(1,1-dimethylethoxy)carbonyl]-L-alanine (11.35 g., 60 mmole) 1-hydroxybenzotriazole hydrate (9.18 g., 60 mmole), and diisopropylethylamine (7.76 g., 60 mmole). The reaction mixture is cooled in an ice bath under nitrogen and treated with dicyclohexylcarbodiimide (12.38 g., 60 mmole), then stirred in the cold for one hour, and allowed to warm to room temperature overnight. The reaction mixture is diluted with ether (150 ml.) and filtered to remove dicyclohexylurea. The filtrate is concentrated in vacuo. The residue is dissolved in ethyl acetate (500 ml.) and this solution is washed with 10% aqueous potassium bisulfate, water, 5% aqueous sodium bicarbonate, water, and brine (100 ml. portions each), dried (MgSO₄), and concentrated in vacuo to give 16.4 g. of crude product. Flash chromatography on Merck 9385 silica gel (400 g.) eluting with petroleum ether:acetone (2:1) gives 12.4 g. of 3-[[(S)-2-[[(1,1-dimethylethoxy)carbonyl]amino]-1-oxopropyl]amino]propanoic acid, methyl ester as a white solid; 73°–76°. TLC (silica gel; petroleum ether:acetone, 2:1) $R_f$=0.37.

Anal. calc'd. for $C_{12}H_{22}N_2O_5$: C, 52.54; H, 8.08; N, 10.21 Found: C, 52.73; H, 8.10; N, 10.21.

(c) 3-[[(S)-2-Amino-1-oxopropyl]amino]propanoic acid, methyl ester, hydrochloride A solution of the methyl ester product from part (b) (12.3 g., 44.8 mmole) in 1.7N hydrogen chloride/acetic acid (132 ml.) is stoppered and stirred at room temperature for 2.5 hours. The solution is concentrated in vacuo. The residue is dissolved in toluene and this solution is concentrated, then the residue is triturated from ether to give 10.3 g. of 3-[[(S)-2-amino-1-oxopropyl]amino]propanoic acid, methyl ester, hydrochloride as an oil. TLC (silica gel; chloroform:methanol:acetic acid, 5:1:1) $R_f$=0.15.

Anal. calc'd. for $C_7H_{15}N_2O_3Cl.0.15$ H₂O: C, 39.41; H, 7.23; N, 13.14: Cl, 16.62 Found: C, 39.41; H, 7.23; N, 12.92; Cl, 16.55.

(d)
3-[[(S)-2-[[Methoxy(2-phenylethyl)phosphinyl]amino]-1-oxopropyl]amino]propanoic acid, methyl ester A solution of the phosphonochloridate prepared in Example 6(d) (about 20 mmole) in dry methylene chloride (32 ml.) is cooled in an ice bath under nitrogen and then treated with a solution of the methyl ester product from part (c) (4.21 g., 20 mmole) and 4-pyrrolidinopyridine (296 mg., 2.0 mmole) in dry methylene chloride (50 ml.). The resulting solution is treated dropwise with a solution of diisopropylethylamine (5.17 g., 40 mmole) in dry methylene chloride (20 ml.), then stirred cold for one hour, and allowed to warm to ambient temperature overnight. The reaction mixture is concentrated in vacuo. The residue is dissolved in ethyl acetate (500 ml.) and this solution is washed with 10% aqueous potassium bisulfate, water, 5% aqueous sodium bicarbonate, water, and brine (100 ml. each), dried (MgSO₄), and concentrated in vacuo to give 4.3 g. of crude product. Flash chromatography on Merck 9385 silica gel (325 g.) eluting with ethyl acetate:methanol (20:1) gives 2.5 g. of 3-[[(S)-2-[[methoxy-(2-phenylethyl)phosphinyl]amino]-1-oxopropyl]amino]propanoic acid, methyl ester as an oil. TLC (silica gel; ethyl acetate:methanol, 10:1) $R_f$=0.39.

Anal. calc'd. for $C_{16}H_{25}N_2O_5P$: C, 53.92; H, 7.07; N, 7.86; P, 8.69 Found: C, 54.15; H, 7.16; N, 7.84; P, 8.5.

(e)
3-[[(S)-2-[[Hydroxy(2-phenylethyl)phosphinyl]amino]-1-oxopropyl]amino]propanoic acid, dilithium salt A solution of the methyl ester product from part (d) (2.4 g., 6.73 mmole) in methanol (50 ml.) is cooled in an ice bath under nitrogen and treated dropwise with 2N lithium hydroxide solution (6.73 ml., 13.47 mmole). After the addition is complete, the reaction mixture is stirred cold for 15 minutes, then allowed to warm to ambient temperature overnight. The reaction mixture is concentrated in vacuo to give 2.3 g. of crude product. Chromatography on a column of HP-20 (5×30 cm.) eluting with water gives 2.0 g. of 3-[[(S)-2-[[hydroxy(2-phenylethyl)phosphinyl]amino]-1-oxopropyl]amino]propanoic acid, dilithium salt as a white solid, m.p. greater than 250°; $[\alpha]_D$=−7.2° (c=0.5, methanol). TLC (silica gel; isopropanol:water:ammonia, 12:2:1) $R_f$=0.26 with heading.

Anal. calc'd. for $C_{14}H_{19}N_2O_5P.2Li.2.1$ H₂O: C, 44.49; H, 6.18; N, 7.41; P, 8.20 Found: C, 44.49; H, 5.85; N, 7.46; P, 8.25.

EXAMPLE 8

4-[[(S)-2-[(Hydroxymethylphosphinyl)amino]-1-oxo-3-phenylpropyl]amino]benzoic acid, dilithium salt (a) 4-Aminobenzoic acid, methyl ester, hydrochloride A stirred suspension of 4-aminobenzoic acid (16.5 g., 120 mmole) in methanol (300 ml.) is cooled to −10° under nitrogen and treated dropwise with thionyl chloride (28.5 g., 240 mmole) while maintaining the temperature between −5° and −10°. After the addition is complete, the reaction mixture is allowed to warm to ambient temperature overnight. The reaction mixture is concentrated in vacuo, and the residue is twice triturated with ether to give 22 g. of 4-aminobenzoic acid, methyl ester, hydrochloride as a light tan solid; m.p. 207° to greater than 250°. TLC (silica gel; n-butanol: acetic acid:water, 4:1:1) $R_f$=0.87.

(b)
4-[[(S)-2-[[(1,1-Dimethylethoxy)carbonyl]amino]-1-oxo-3-phenylpropyl]amino]benzoic acid, methyl ester A solution of 4-aminobenzoic acid, methyl ester, hydrochloride (3.75 g., 20 mmole) in dry dimethylformamide (25 ml.) is treated with N-[(1,1-dimethylethoxy)carbonyl]-L-phenylalanine (5.3 g., 20 mmole), 1-hydroxybenzotriazole hydrate (3.05 g., 20 mmole) and diisopropylethylamine (2.6 g., 20 mmole). The reaction mixture is cooled in an ice bath under nitrogen and treated with dicyclohexylcarbodiimide (4.13 g., 20 mmole), then stirred cold for one hour, and then allowed to warm to ambient temperature overnight. The reaction mixture is diluted with ether (150 ml.) and filtered to remove dicyclohexylurea. The filtrate is concentrated in vacuo. The residue is dissolved in ethyl acetate (150 ml.) and washed with 10% aqueous potassium bisulfate, water, 5% aqueous sodium bicarbonate, water, and brine (30 ml. each), dried (MgSO$_4$), and concentrated in vacuo to give 9.2 g. of crude product. One recrystallization from hot methylene chloride gives 5.5 g. of partially purified material and 3.3 g. of impure material. The impure material is recrystallized again from hot methylene chloride to yield an additional 1.2 g. of partially purified material and 2.0 g. of impure material. Flash chromatography of the impure material on Merck 9385 silica gel (95 g.) eluting with hexanes:ethyl acetate (3:1) gives 1.5 g. of partially purified material. A total of 7.2 g. of the partially purified material is combined with 1.5 g. of product of similar purity from another run and the entire 8.7 g. is recrystallized from hot ethyl acetate:-hexanes to give 4.9 g. of 4-[[(S)-2-[[(1,1-dimethylethoxy)carbonyl]amino]-1-oxo-3-phenylpropyl]amino]benzoic acid, methyl ester; m.p. 173°–175°. TLC (silica gel; hexanes:ethyl acetate, 2:1) R$_f$=0.33 (trace at origin).

Anal. calc'd. for C$_{22}$H$_{26}$N$_2$O$_5$: C, 66.31; H, 6.58; N, 7.03 Found: C, 66.60; H, 6.52; N, 7.04.

(c)

4-[[(S)-2-Amino-1-oxo-3-phenylpropyl]amino]benzoic acid, methyl ester, hydrochloride A solution of the methyl ester product from part (b) (4.8 g., 12 mmole) in 1.7N hydrogen chloride/acetic acid (36 ml.) is stoppered and stirred at room temperature for 4 hours. The solution is concentrated in vacuo, and the residue is triturated from ether to give 3.93 g. of 4-[[(S)-2-amino-1-oxo-3-phenylpropyl]amino]benzoic acid, methyl ester, hydrochloride. TLC (silica gel; chloroform:methanol:acetic acid, 10:1:1) R$_f$=0.38.

Anal. calc'd. for C$_{17}$H$_{19}$N$_2$O$_3$Cl.0.3H$_2$O: C, 60.08; H, 5.80; N, 8.24; Cl, 10.43 Found: C, 60.08; H, 5.78; N, 8.26; Cl, 10.43.

(d)

4-[[(S)-2-[[(Methoxy)methylphosphinyl]amino]-1-oxo-3-phenylpropyl]amino]benzoic acid, methyl ester The hydrochloride product from part (c) (3.72 g., 11.12 mmole) is partitioned between ethyl acetate and 5% aqueous sodium bicarbonate (200 ml. each). The organic layer is washed with brine and dried (MgSO$_4$) to give 3.3 g. of 4-[[(S)-2-amino-1-oxo-3-phenylpropyl]amino]benzoic acid, methyl ester.

A solution of distilled dimethyl methylphosphonate (3.0 g., 24.2 mmole) in dry ether (36 ml.) is cooled in an ice bath under nitrogen and treated dropwise with a solution of oxalyl chloride (4.6 g., 36.4 mmole) in dry ether (4 ml.), then allowed to warm to ambient temperature overnight. The ether is removed under low vacuum, and the residue is distilled in vacuo. The fraction boiling at 75°–120° at a pressure range of 1.0 to 5.0 mm of Hg is collected to give 1.63 g. of the phosphonochloridate as a clear, colorless oil.

A solution of this phosphonochloridate (1.6 g., 12.45 mmole) in dry methylene chloride (15 ml.) is cooled in an ice bath under nitrogen and treated dropwise with a solution of 4-[[(S)-2-amino-1-oxo-3-phenylpropyl]amino]benzoic acid, methyl ester (3.3 g., 11.12 mmole) and 4-pyrrolidinopyridine (165 mg., 1.11 mmole) in dry methylene chloride (15 ml.), followed by a solution of diisopropylethylamine (1.43 g., 11.12 mmole) in dry methylene chloride (15 ml.). The reaction mixture is stirred cold for one hour and then allowed to warm to room temperature overnight. The reaction mixture is concentrated in vacuo, and the residue is dissolved in ethyl acetate (500 ml.) and washed with 10% aqueous potassium bisulfate, water, 5% aqueous sodium bicarbonate, water, and brine (100 ml. each), dried (MgSO$_4$), and concentrated in vacuo to give 4.0 g. of crude product. Flash chromatography on Merck 9385 silica gel (400 g.) eluting with toluene:acetic acid (6:1) gives 2.9 g. of 4-[[(S)-2-[[(methoxy)methylphosphinyl]amino]-1-oxo-3-phenylpropyl]amino]benzoic acid, methyl ester. TLC (silica gel; toluene:acetic acid, 4:1) R$_f$=0.36.

Anal. calc'd. for C$_{19}$H$_{23}$N$_2$O$_5$P: C, 58.46; H, 5.93; N, 7.18; P, 7.93 Found: C, 58.61; H, 5.88; N, 7.09; P, 7.7.

(e)

4-[[(S)-2-[(hydroxymethylphosphinyl)amino]-1-oxo-3-phenylpropyl]amino]benzoic acid, dilithium salt A solution of the methyl ester product from part (d) (2.5 g., 6.4 mmole) in methanol (45 ml.) is cooled in an ice bath under nitrogen and treated dropwise with 2N lithium hydroxide solution (9.6 ml., 19.2 mmole). After the addition is complete, the reaction mixture is stirred cold for 15 minutes, then allowed to warm to ambient temperature overnight. The reaction mixture is concentrated in vacuo to give 3.0 g. of crude product. The crude product is purified by chromatography in several batches on an HP-20 column (2.5×20 cm.) packed in and eluted with water to give 2.33 g. of partially purified product. Chromatography on a column of LH-20 (5×30 cm.) packed in and eluted with water gives 2.0 g. of 4-[[(S)-2-[(hydroxymethylphosphinyl)amino]-1-oxo-3-phenylpropyl]amino]benzoic acid, dilithium salt as a white solid; m.p. greater than 250°; [α]$_D$=−70° (c=0.5, methanol). TLC (silica gel; isopropanol: water:ammonia, 12:2:1) R$_f$=0.22 with heading (trace at 0.61).

Anal. calc'd. for C$_{17}$H$_{17}$N$_2$O$_5$P.2Li.1.4 H$_2$O: C, 51.13; H, 5.00; N, 7.02; P, 7.76 Found: C, 51.13; H, 4.79; N, 6.99; P, 7.7.

EXAMPLE 9

4-[[(S)-2-[[Hydroxy(2-phenylethyl)phosphinyl]amino]-1-oxopropyl]amino]benzoic acid, dilithium salt (a)

4-[[(S)-2-[[(1,1-Dimethylethoxy)carbonyl]amino]-1-oxopropyl]amino]benzoic acid, methyl ester A solution of 4-aminobenzoic acid, methyl ester, hydrochloride (8.52 g., 45.4 mmole) in dry dimethylformamide (55 ml.) is treated with N-[(1,1-dimethylethoxy)-carbonyl]-L-alanine (8.6 g., 45.4 mmole), 1-hydroxybenzotriazole hydrate (6.95 g., 45.4 mmole), and diisopropylethylamine (5.87 g., 45.4 mmole). The resulting solution is cooled in an ice bath under nitrogen and treated with dicyclohexylcarbodiimide (9.37 g., 45.4 mmole), then stirred cold for one hour, and allowed to warm to ambient temperature overnight. The reaction mixture is diluted with ether (150 ml.) and filtered to remove dicyclohexylurea, and the filtrate is concentrated in vacuo. The residue is diluted with ethyl acetate (500 ml.) and this solution is washed with 10% aqueous potassium bisulfate, water, 5% aqueous sodium bicarbonate, water, and brine (100 ml. each), dried (MgSO$_4$), and concentrated in vacuo to yield 14.9 g. of crude product. The crude material is purified by treatment with methylene chloride (60 ml.) and the insoluble material is filtered to give 5.5 g. of 4-[[(S)-2 -[[(1,1-dimethylethoxy)carbonyl]amino]-1-oxopropyl]amino]benzoic acid, methyl ester as a white solid; 186°–188°. TLC (silica gel; hexanes:ethyl acetate, 2:1) $R_f$=0.26.

(b) 4-[[(S)-2-Amino-1-oxopropyl]amino]benzoic acid, methyl ester, hydrochloride

A solution of the methyl ester product from part (a) (5.4 g., 16.75 mmole) in 1.7N hydrogen chloride/acetic acid (50 ml.) is stoppered and stirred at room temperature for 6 hours. The solution is concentrated in vacuo and the residue is triturated with ether to give 4.2 g. of 4-[[(S)-2-amino-1-oxopropyl]amino]benzoic acid, methyl ester, hydrochloride; m.p. greater than 250°. TLC (silica gel; chloroform:methanol:acetic acid, 5:1:1) $R_f$=0.38.

Anal. calc'd. for $C_{11}H_{15}N_2O_3Cl$: C, 51.06; H, 5.84; N, 10.83; C, 13.71 Found: C, 50.86; H, 5.80; N, 10.75; C, 13.47.

(c) 4-[[(S)-2-[[Methoxy(2-phenylethyl)phosphinyl]amino]-1-oxopropyl]amino]benzoic acid, methyl ester A solution of the phosphonochloridate prepared in Example 6(d) (about 16.1 mmole) in dry methylene chloride (25 ml.) is cooled in an ice bath under nitrogen, then treated with a solution of the methyl ester product from part (b) (4.15 g., 16.10 mmole) and 4-pyrrolidinopyridine (239 mg., 1.61 mmole) in dry methylene chloride (45 ml.). The resulting solution is treated dropwise with a solution of diisopropylethylamine (4.16 g., 32.2 mmole) in dry methylene chloride (18 ml.), then stirred cold for one hour and allowed to warm to ambient temperature overnight. The reaction mixture is concentrated in vacuo. The residue is dissolved in ethyl acetate (400 ml.) and this solution is washed with 10% aqueous potassium bisulfate, water, 5% aqueous sodium bicarbonate, water, and brine (75 ml. each), dried (MgSO$_4$), and concentrated in vacuo to yield 5.3 g. of crude product. Flash chromatography on Merck 9385 silica gel (400 g.) eluting with ethyl acetate:methanol (80:1) gives 4.15 g. of 4-[[(S)-2-[[methoxy(2-phenylethyl)phosphinyl]amino]-1-oxopropyl]amino]benzoic acid, methyl ester. TLC (silica gel; ethyl acetate: methanol, 20:1) $R_f$=0.44 and 0.48 (diastereomers). Anal. calc'd. for $C_{20}H_{25}N_2O_5P \cdot 0.28 H_2O$: C, 58.67; H, 6.29; N, 6.84; P, 7.56 Found: C, 59.05; H, 6.36; N, 6.42; P, 7.83.

(d) 4-[[(S)-2-[[Hydroxy(2-phenylethyl)phosphinyl]amino]-1-oxopropyl]amino]benzoic acid, dilithium salt A solution of the methyl ester product from part (c) (2.2 g., 5.44 mmole) in methanol (36 ml.) is cooled in an ice bath under nitrogen and treated dropwise with 2N lithium hydroxide solution (8.16 ml., 16.32 mmole). After the addition is complete, the reaction mixture is stirred cold for 15 minutes, and then allowed to warm to ambient temperature overnight. The reaction mixture is concentrated in vacuo to yield 3.5 g. of crude product. The crude material is combined with 1.6 g. of product from another run and the entire 5.1 g. is chromatographed on a column of HP-20 resin (5×25 cm.) eluting with a gradient from 500 ml. of water to 500 ml. of acetonitrile to give 1.55 g. 4-[[(S)-2-[[hydroxy(2-phenylethyl)phosphinyl]amino-1-oxopropyl]amino]-benzoic acid, dilithium salt as a white solid; m.p. greater than 250°; $[\alpha]_D$= −52.0° (c=0.5, methanol). TLC (silica gel; isopropanol: water:ammonia, 12:2:1) $R_f$=0.32 with heading. Anal. calc'd. for $C_{18}H_{19}N_2O_5P \cdot 2Li \cdot$ 2.35 H$_2$O: C, 50.21; H, 5.55; N, 6.51; P, 7.19 Found: C, 50.19; H, 5.71; N, 6.69; P. 6.97.

EXAMPLE 10

4-[[(S)-2-[(Hydroxymethylphosphinyl)oxy]-1-oxo-3-phenylpropyl]amino]benzoic acid, dilithium salt (a) 4-[[(S)-2-Hydroxy-1-oxo-3-phenylpropyl]amino]benzoic acid, methyl ester (S)-2-Hydroxy-3-phenylpropanoic acid (500 mg., 3.01 mmole) and 4-aminobenzoic acid, methyl ester (455 mg., 3.01 mmole) are dissolved in dimethylformamide (5 ml.) at room temperature under argon. 1-Hydroxybenzotriazole hydrate (405 mg., 3.01 mmole) is added, and the resulting mixture is cooled to 0°. Dicyclohexylcarbodiimide (620 mg., 3.01 mmole) is added and the mixture is stirred at 0° for one hour. The mixture is allowed to warm to room temperature and is stirred overnight. The volatiles are evaporated, and the residue is dissolved in ethyl acetate and filtered to remove dicyclohexylurea. The organic layer is extracted with 5% potassium bisulfate, saturated aqueous sodium bicarbonate, and brine, dried (Na$_2$SO$_4$), and filtered. The volatiles are evaporated and the crude residue is combined with product of similar purity from another run. Purification by trituration with methylene chloride gives 3.7 g. of 4-[[(S)-2-hydroxy-1-oxo-3-phenylpropyl]amino]benzoic acid, methyl ester.

(b) 4-[[(S)-2-[[(Methoxy)methylphosphinyl]oxy]-1-oxo-3-phenylpropyl]amino]benzoic acid, methyl ester The phosphonochloridate from Example 8(d) (1.8 g., 13.9 mmole) is dissolved in methylene chloride (17 ml.) at room temperature under argon. The mixture is cooled to 0°, and a suspension of the methyl ester product from part (a) (3.7 g., 12.37 mmole) and 4-pyrrolidinopyridine (185 mg., 1.24 mmole) in methylene chloride (17 ml.) is added dropwise. Diisopropylethylamine (2.15 ml., 12.37 mmole) is added dropwise, and the resulting mixture is stirred at 0° for one hour. The mixture is allowed to warm to room temperature and stirred overnight. The volatiles are evaporated, and the residue is partitioned between ethyl acetate and 5% potassium bisulfate. The organic layer is extracted once with 5% sodium bicarbonate and once with brine, dried (Na$_2$SO$_4$), filtered, and the volatiles are evaporated. The residue is purified by trituration with ether to give 2.5 g. of 4-[[(S)-2-[[(methoxy)methylphosphinyl]oxy]-1-oxo-3-phenylpropyl]amino]benzoic acid, methyl ester. TLC (silica gel; methylene chloride:acetic acid:methanol, 20:1:1) $R_f$=0.78.

(c) 4-[[(S)-2-[(Hydroxymethylphosphinyl)oxy]-1-oxo-3-phenylpropyl]amino]benzoic acid, methyl ester The methyl ester product from part (b) (2.3 g., 5.88 mmole) is suspended in acetone (7 ml.) at room temperature. Trimethylamine is bubbled in for about 20 minutes to saturate the mixture. The reaction vessel is sealed, and the mixture is heated to about 95° and is stirred overnight. The volatiles are evaporated, and the residue is partitioned between ethyl acetate and 5% potassium bisulfate. The organic layer is washed once with brine, dried (Na$_2$SO$_4$), filtered, and the volatiles are evaporated to give 1.86 g. of 4-[[(S)-2=[(hydroxymethylphosphinyl)oxy]-1-oxo-3-phenylpropyl]amino]- benzoic acid, methyl ester. TLC (silica gel; isopropanol-:ammonia:water, 7:2:1) $R_f=0.62$.

(d)

4-[[(S)-2-[(Hydroxymethylphosphinyl)oxy]-1-oxo-3-phenylpropyl]amino]benzoic acid, dilithium salt The methyl ester product from part (c) (1.86 g., 4.93 mmole) is dissolved in methanol (11 ml.) at room temperature under argon. 1N Lithium hydroxide (10.5 ml., 10.5 mmole) is added, and the resulting mixture is stirred overnight. The volatiles are evaporated, and the residue is purified by column chromatography on HP-20 eluting with water to yield upon lyophilization 1.57 g. of 4-[[(S)-2-[(hydroxymethylphosphinyl)oxy]-1-oxo-3-phenylpropyl]amino]benzoic acid, dilithium salt as a solid; m.p. 200°-210° (dec.); $[\alpha]_D = -90°$ (c=0.9, water). TLC (silica gel; isopropanol:ammonia:water, 7:2:1) $R_f=0.51$.

Anal. calc'd. for $C_{17}H_{16}NO_6P.2Li.0.64H_2O$: C, 52.79; H, 4.51; N, 3.62; P, 8.01 Found: C, 52.94; H, 4.83; N, 3.60; P, 7.79.

EXAMPLE 11

(S)-3-[[2-[(Hydroxymethylphosphinyl)amino]-1-oxo-3-phenylpropyl]amino]benzoic acid, dilithium salt (a) 3-Aminobenzoic acid, methyl ester, hydrochloride A stirred suspension of 3-aminobenzoic acid (10.0 g., 72.9 mmole) in methanol (200 ml.) is cooled to −10° and treated dropwise with thionyl chloride (17.3 g., 146 mmole) while keeping the temperature below −5°. After the addition is completed, the reaction mixture is allowed to warm to ambient temperature overnight. The mixture is concentrated in vacuo, and the residue is twice triturated with ether to give 13.2 g. of 3-aminobenzoic acid, methyl ester, hydrochloride as a white solid; m.p. 207°-216°. TLC (silica gel; chloroform:methanol:acetic acid; 18:1:1) $R_f=0.70$.

(b)

3-[[(S)-2-[[(1,1-Dimethylethoxy)carbonyl]amino]-1-oxo-3-phenylpropyl]amino]benzoic acid, methyl ester A solution of 3-aminobenzoic acid, methyl ester, hydrochloride (1.58 g., 8.43 mmole) in dry dimethylformamide (10 ml.) is treated with N-[(1,1-dimethylethoxy)-carbonyl-L-phenylalanine (2.24 g., 8.43 mmole), 1-hydroxybenzotriazole (1.14 g., 8.43 mmole), and distilled diisopropylethylamine (1.09 g., 8.43 mmole). The reaction mixture is cooled in an ice bath under nitrogen and treated with dicyclohexylcarbodiimide (1.74 g., 8.43 mmole). The reaction mixture is stirred cold for one hour, then is allowed to warm to ambient temperature overnight. The reaction mixture is diluted with ether (75 ml.) and filtered to remove dicyclohexylurea. The filtrate is concentrated in vacuo. The residue is dissolved in ethyl acetate (75 ml.) and the solution is washed with 10% potassium bisulfate, water, 5% sodium bicarbonate, water and brine (20 ml. portions), dried (MgSO₄), and concentrated in vacuo to give 4.0 g. of crude product. Flash chromatography on Merck 9385 silica gel (400 g.) eluting with hexanes:ethyl acetate (4:1) gives 2.20 g. of 3-[[(S)-2-[[(1,1-dimethylethyoxy)carbonyl]amino]-1-oxo-3-phenylpropyl]amino]-benzoic acid, methyl ester as a white solid; m.p. 62°-66°. TLC (silica gel; hexanes:ethyl acetate; 2:1) $R_f=0.32$.

Anal. calc'd. for $C_{22}H_{26}H_2O_5.0.23H_2O$: C, 65.63; H, 6.63; N, 6.96 Found: C, 65.63; H, 6.66; N, 6.94.

(c)

3-[[(S)-2-Amino-1-oxo-3-phenylpropyl]amino]benzoic acid, methyl ester, hydrochloride A solution of the methyl ester product from part (b) (2.1 g., 5.27 mmole) in 1.7N hydrogen chloride/acetic acid (16 ml.) is stoppered and stirred at ambient temperature for 4 hours. The reaction mixture is concentrated in vacuo and the residue is triturated with ether to give 1.65 g. of 3-[[(S)-2-amino-1-oxo-3-phenylpropyl]amino]-benzoic acid, methyl ester, hydrochloride as a white solid; m.p. 93°-135° (decomposes). TLC (silica gel; chloroform:methanol:acetic acid, 10:1:1) $R_f=0.43$.

Anal. calc'd. for $C_{17}H_{18}N_2O_3.1.07HCl.0.02H_2O$: C, 60.46; H, 5.70; N, 8.29; Cl, 11.23 Found: C, 60.50; H, 6.32; N, 8.08; Cl, 11.24.

(d)

(S)-3-[[2-[(Methoxymethylphosphinyl)amino]-1-oxo-3-phenylpropyl]amino]benzoic acid, methyl ester The hydrochloride product from part (c) (1.61 g., 4.81 mmole) is partitioned between ethyl acetate and 5% aqueous sodium bicarbonate (100 ml. each). The organic layer is separated, washed with brine, dried (MgSO₄), and concentrated in vacuo to give 3-[[(S)-2-amino-1-oxo-3-phenylpropyl]amino]benzoic acid, methyl ester.

A solution of methyl methylphosphonyl chloride (680 mg., 5.29 mmole) [prepared as described in Example 8 (d)] in dry methylene chloride (7 ml.) is treated with 4-pyrrolidinopyridine (71 mg., 0.48 mmole). The reaction mixture is cooled in an ice bath under nitrogen and treated with a solution of 3-[[(S)-2-amino-1-oxo-3-phenylpropyl]amino]benzoic acid, methyl ester in dry methylene chloride (7 ml.), followed by a solution of diisopropylethylamine (621 mg., 4.81 mmole) in dry methylene chloride (7 ml.). The reaction mixture is stirred cold for one hour and then allowed to come to ambient temperature overnight. After 21 hours, an additional 1.1 equivalent of the phosphonochloridate (680 mg., 5.29 mmole) and 1 equivalent of diisopropylethylamine (621 mg., 4.81 mmole) are added and the mixture is allowed to continue stirring at room temperature. After a total reaction time of 24 hours, the solvent is removed in vacuo. The residue is dissolved in ethyl acetate (200 ml.) and this solution is washed with 50 ml. portions of 10% potassium bisulfate, water, 5% sodium bicarbonate, water, and brine, dried (MgSO₄), and concentrated in vacuo to give 1.52 g. of crude product. Flash chromatography on Merck silica gel 9385 eluting with toluene:acetic acid (10:1) gives 800 mg. of (S)-3-[[2-[(methoxymethylphosphinyl)amino]-1-oxo-3-phenylpropyl]amino]benzoic acid, methyl ester as a white solid; 178°-182°. TLC (silica gel; toluene:acetic acid, 5:1) $R_f=0.38$ (minor impurity at $R_f=0.43$).

Anal. calc'd. for $C_{19}H_{23}N_2O_5P$: C, 58.46; H, 5.94; N, 7.18; P, 7.93 Found: C, 58.46; H, 5.99; N, 7.15; P, 7.58.

(e)

(S)-3-[[2-[(Hydroxymethylphosphinyl)amino]-1-oxo-3-phenylpropyl]amino]benzoic acid, dilithium salt A solution of the methyl ester product from part (d) (750 mg., 1.92 mmole) in methanol (15 ml.) is cooled in an ice bath under nitrogen and treated dropwise with 1N lithium hydroxide solution (5.76 ml., 5.76 mmole). The reaction mixture is stirred at 0° for 15 minutes, and then allowed to come to ambient temperature overnight. The reaction mixture is concentrated in vacuo to give 830 mg. of crude product. Two chromatographies on a 5×25 cm column of HP-20 resin, eluting with water, gives 507 mg. of (S)-3-[[2-[(hydroxymethylphosphinyl)amino]-1-oxo-3-phenylpropyl]amino]benzoic acid, dilithium salt; m.p. greater than 250°; [α]$_D$= −57.2° (c=0.5, methanol). TLC (silica gel, isopropanol:water:NH₄OH, 12:2:1) R$_f$=0.31 with heading.

Anal. calc'd. for C$_{17}$H$_{17}$N$_2$O$_5$P . 2Li . 2H$_2$O: C, 49.83; H, 5.15; N, 6.84; P, 7.56 Found: C, 49.89; H, 4.85; N, 6.82; P, 7.62.

EXAMPLE 12

(S)-4-[[2-[[Hydroxy(4-phenylbrtyl)phosphinyl]oxy]-1-oxo-3-phenylpropyl]amino]benzoic acid, methyl ester A solution of (4-phenylbutyl)phosphinic acid (900 mg., 4.54 mmole) [prepared as described in Example 4(a) of U.S. Pat. No. 4,745,196] and 4-[[(S)-2-hydroxy-1-oxo-3-phenylpropyl]amino]benzoic acid, methyl ester (876 mg., 2.93 mmole) [prepared as described in Example 10(a)] in tetrahydrofuran (13 ml.) is treated with dicyclohexylcarbodiimide (1.16 g., 5.6 mmole) and 4-dimethylaminopyridine (142 mg., 1.16 mmole), and the reaction mixture is stirred at ambient temperature for 2.5 hours. The reaction mixture is filtered to remove dicyclohexylurea and the filter cake is washed well with ethyl acetate. The filtrate is washed with 5% potassium bisulfate, saturated sodium bicarbonate, and brine, dried (Na$_2$SO$_4$), and concentrated in vacuo. The residue is triturated several times with ether to precipitate unreacted starting material which is filtered off. The filtrate is concentrated in vacuo to give 1.2 g. of crude . phosphonous ester product.

A solution of this phosphonous ester in p-dioxane (7 ml.) under argon is treated with a solution of sodium periodate (752 mg., 3.51 mmole) in water (7 ml.), and the mixture is stirred at ambient temperature overnight. The reaction mixture is partitioned between ethyl acetate and 5% potassium bisulfate. The aqueous layer is separated and extracted once more with ethyl acetate. The combined organic extract is treated with 5% potassium bisulfate and aqueous sodium bisulfite until the iodine color is discharged. The organic layer is washed with brine, dried (Na$_2$SO$_4$), and concentrated in vacuo. The residue is dissolved in ether, and some starting material that precipitates is removed by filtration. The filtrate is concentrated in vacuo, and the residue is dissolved in ethyl acetate and treated with a solution of adamantanamine (488 mg., 3.22 mmole) in ether (33 ml.). The resulting precipitate is filtered and then partitioned between ethyl acetate and 1N HCl. The organic layer is dried (Na$_2$SO$_4$) and concentrated in vacuo. The residue is recrystallized from ethyl acetate to give 725 mg. of a white solid. A portion of this material (135 mg.) is recrystallized once more from ethyl acetate to give 85 mg. of white solid (S)-4-[[2-[[hydroxy(4-phenylbutyl)phosphinyl]oxy]-1-oxo-3-phenylpropyl]amino]benzoic acid, methyl ester; m.p. 150°-154° ; [α]$_D$= −40.4° (c=0.5, methanol). TLC (silica gel; dichloromethane:methanol:acetic acid, 20:1:1) R$_f$=0.31.

Anal. calc'd. for C$_{27}$H$_{30}$NO$_6$P.0.18H$_2$O: C, 65.02; H, 6.14; N, 2.81; P, 6.21 Found: C, 65.00; H, 6.12; N, 2.83; P, 6.31.

EXAMPLE 13

(S)-4-[[2-[[Hydroxy(4-phenylbutyl)phosphinyl]oxy]-1-oxo-3-phenylpropyl]amino]benzoic acid, dilithium salt A suspension of the methyl ester product of Example 12 (590 mg., 1.19 mmole) in methanol (5 ml.) at ambient temperature under argon is treated with 1N lithium hydroxide (2.53 ml., 2.53 mmole), and the reaction mixture is allowed to stir overnight. The reaction mixture is concentrated in vacuo, the residue is redissolved in water, and the pH of the solution is adjusted to 1 with concentrated HCl. The resulting white precipitate is collected to give 445 mg. of crude diacid product; m.p. 183°-188°. TLC (silica gel; isopropanol: NH₄OH:water, 9:2:1) R$_f$=0.47.

The diacid is dissolved in a minimal volume of methanol. Water is added until the solution begins to cloud. This solution is treated with 2N lithium hydroxide (0.87 ml., 1.74 mmole) to form the dilithium salt. The solution is concentrated in vacuo. The residue is dissolved in a minimal volume of water and chromatographed on a 2.5×20 cm. HP-20 column, packed in water, and eluted with a gradient from 500 ml. of water to 500 ml. of acetonitrile. The product containing fractions are collected and lyophilized from water to give 250 mg. of white solid (S)-4-[[2-[[hydroxy(4-phenylbutyl)phosphinyl]oxy]-1-oxo-3-phenylpropyl]amino]benzoic acid, dilithium salt; m.p. greater than 250° ; [α]$_D$= −95.4° (c=1, methanol). TLC (silica gel; isopropanol:NH₄OH:water, 9:2:1) R$_f$=0.57.

Anal. calc'd. for C$_{26}$H$_{26}$NO$_6$P . 2Li . 1.61 H$_2$O: C, 59.78; H, 5.64; N, 2.68; P, 5.93 Found: C, 59.89; H, 5.60; N, 2.57; P, 5.68.

EXAMPLES 14-51

Following the above procedures, additional compounds of the formula

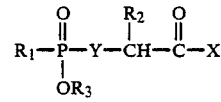

are prepared.

| Example | R₁ | R₃ | Y | R₂ | X |
|---|---|---|---|---|---|
| 14 | phenyl-(CH₂)₄- | H | O | -CH₂-CH(CH₃)₂ | -NH-(CH₂)₃-C(=O)-OH |
| 15 | phenyl-(CH₂)₄- | H | NH | phenyl-CH₂- | -NH-(CH₂)₄-C(=O)-OH |
| 16 | phenyl-(CH₂)₂- | H | O | cyclohexyl-CH₂- | -NH-(CH₂)₅-C(=O)-OH |
| 17 | phenyl- | H | NH | -CH₃ | -NH-(CH₂)₆-C(=O)-OH |
| 18 | cyclohexyl-CH₂- | H | O | phenyl-(CH₂)₂- | -NH-(CH₂)₇-C(=O)-OH |
| 19 | thienyl-CH₂- | H | NH | imidazolyl-CH₂- | -NH-(CH₂)₈-C(=O)-OH |
| 20 | furyl-CH₂- | H | O | indolyl-CH₂- | -NH-(CH₂)₉-C(=O)-OH |
| 21 | pyridyl-(CH₂)₂- | H | NH | phenyl-CH₂- | -NH-(CH₂)₁₀-C(=O)-OH |

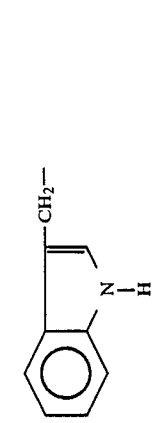

-continued

| Example | R₁ | R₃ | Y | R₂ | X |
|---|---|---|---|---|---|
| 27 | cyclopentyl-CH₂— | H | NH | —CH₃ | —NH—CH—CH₂—C(=O)—OH, with CH₂—S—CH₃ |
| 28 | phenyl-(CH₂)₄— | H | O | —CH(CH₃)₂ | —NH—CH—(CH₂)₂—C(=O)—OH, with CH₃ |
| 29 | phenyl-(CH₂)₄— | H | O | —CH₂-(α-naphthyl) | —NH—(CH₂)₂—C(=O)—OH |
| 30 | H₃C— | H | O | —(CH₂)₄—C(=O)—NH₂ | —NH—(CH₂)₂—C(=O)—OH |
| 31 | H₃C— | H | NH | —CH₂-(β-naphthyl) | —NH—C₆H₄—COOH (meta) |
| 32 | H₃C— | H | O | —CH₂—phenyl | —NH—C₆H₄—COOH (ortho) |
| 33 | phenyl-(CH₂)₄— | H | NH | —CH₂—phenyl | —NH—C₆H₄—COOH (ortho) |
| 34 | phenyl-(CH₂)₂— | H | O | —CH₂—phenyl | —NH—C₆H₄—COOH (meta) |

-continued

| Example | R₁ | R₃ | Y | R₂ | X |
|---|---|---|---|---|---|
| 42 | H₃C— | H | NH | —CF₃ | —NH—⟨C₆H₄⟩—COOH (para) |
| 43 | ⟨C₆H₅⟩—(CH₂)₄— | H | O | —CF₃ | —NH—(CH₂)₂—COOH |
| 44 | ⟨C₆H₅⟩—(CH₂)₄— | H | O | —CF₃ | —NH—CH(CH₂-(α-naphthyl))—CH₂—COOH |
| 45 | ⟨C₆H₅⟩—(CH₂)₄— | H | O | —CH₃ | —NH—CH(CH₂-(β-naphthyl))—CH₂—COOH |
| 46 | H₃C— | H | NH | —CH₂—CH(CH₃)₂ | —NH—⟨C₆H₄⟩—COOH (para) |
| 47 | H₃C— | H | NH | —CH₂-(α-naphthyl) | —NH—⟨C₆H₄⟩—COOH (para) |
| 48 | ⟨C₆H₅⟩—(CH₂)₂— | H | NH | —CH₂-(β-naphthyl) | —NH—(CH₂)₃—COOH |
| 49 | ⟨biphenyl⟩—CH₂— | H | NH | —(CH₂)₂—CH₃ | —NH—⟨C₆H₄⟩—COOH (meta) |

-continued

| Example | R₁ | R₃ | Y | R₂ | X |
|---|---|---|---|---|---|
| 50 | (α-naphthyl)-CH₂— | H | NH | —CH₂—CH(CH₃)₂ | —NH—C₆H₄—COOH |
| 51 | (β-naphthyl)-CH₂— | H | NH | —CH₂—CH(CH₃)₂ | —NH—C₆H₄—COOH |

EXAMPLE 52

1000 tablets each containing the following ingredients:

| | |
|---|---|
| 4-[[(S)-2-[(Hydroxymethylphosphinyl)-amino]-1-oxo-3-phenylpropyl]amino]-benzoic acid, dilithium salt | 100 mg. |
| Cornstarch | 50 mg. |
| Gelatin | 7.5 mg. |
| Avicel (microcrystalline cellulose) | 25 mg. |
| Magnesium stearate | 2.5 mg. |
| | 180 mg. | are prepared from sufficient bulk quantities by mixing the product of Example 8 and cornstarch with an aqueous solution of the gelatin. The mixture is dried and ground to a powder. The Avicel and then the magnesium stearate are admixed with granulation. This mixture is then compressed in a tablet press to form 1000 tablets each containing 100 mg. of active ingredient. This same procedure can be employed to prepare tablets containing 50 mg. of active ingredient.

Similarly, tablets containing 50 mg or 100 mg. of the product of any of Examples 1 to 7 and 9 to 51 can be prepared.

EXAMPLE 53

Two piece #1 gelatin capsules are filled with a mixture of the following ingredients:

| | |
|---|---|
| 3-[[(S)-2-[[Hydroxy(2-phenylethyl)-phosphinyl]amino]-1-oxo-3-phenyl-propyl]amino]propanoic acid, dilithium salt | 100 mg. |
| Magnesium stearate | 7 mg. |
| Lactose | 193 mg. |
| | 300 mg. |

In a similar manner, capsules containing 100 mg. of the product of any of Examples 1 to 5 and 7 to 51 can be prepared.

EXAMPLE 54

An injectable solution is prepared as follows:

| | |
|---|---|
| 3-[[(S)-2-[[Hydroxy(phenylmethyl)-phosphinyl]oxy]-1-oxo-3-phenyl-propyl]amino]propanoic acid, dilithium salt | 500 g. |
| Methyl paraben | 5 g. |
| Propyl paraben | 1 g. |
| Sodium chloride | 25 g. |
| Water for injection | 5 l. |

The active substance, preservatives and sodium chloride are dissolved in 3 liters of water for injection and then the volume is brought up to 5 liters. The solution is filtered through a sterile filter and aseptically filled into presterilized vials with rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1, 2, and 4 to 51.

What is claimed is:

1. A compound of the formula $$R_1-\overset{O}{\underset{OR_3}{P}}-NH-\overset{R_2}{\underset{}{CH}}-\overset{O}{C}-X$$

including a pharmaceutically acceptable salt thereof wherein:

$R_1$ is straight or branched alkyl of 1 to 4 carbons or $-(CH_2)_q-\phenyl$ ;

$R_2$ is straight or branched chain alkyl of 1 to 4 carbons, trifluoromethyl, or $-CH_2-\phenyl$ ;

X is $-NH-\phenyl-COOR_5$ or $-NH-\phenyl-COOR_5$ ;

$R_3$ and $R_5$ are independently selected from the group consisting of hydrogen, straight or branched chain alkyl of 1 to 4 carbons, and an alkali metal salt ion; and q is an integer from 1 to 4.

2. A compound of the formula $$R_1-\overset{O}{\underset{OR_3}{P}}-NH-\overset{R_2}{\underset{}{CH}}-\overset{O}{C}-X$$

including a pharmaceutically acceptable salt thereof wherein:

$R_1$ is straight or branched chain alkyl of 1 to 4 carbons or $-(CH_2)_q-\phenyl$ ;

$R_2$ *is straight or branched alkyl of* 1 to 4 carbons, trifluoromethyl, or $-CH_2-\phenyl$ ;

X is $-NH-(CH_2)_2-COOR_5$;

$R_3$ and $R_5$ are independently selected from the group consisting of hydrogen, straight or branched chain alkyl of 1 to 4 carbons, and an alkali metal salt ion; and q is an integer from 1 to 4.

3. A compound of claim 2 wherein:

$R_1$ is

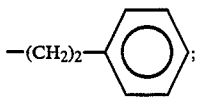

and $R_2$ is methyl.

4. The compound of claim 3, 4-[[(S)-2-[[hydroxy(2-phenylethyl)phosphinyl]amino]-1-oxo-propyl]amino]-benzoic acid, dilithium salt.

5. A compound of claim 1 wherein:

$R_1$ is methyl; and $R_2$ is

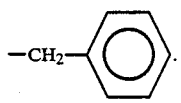

6. The compound of claim 5, 4-[[(S)-2-[(hydroxymethylphosphinyl)amino]-1-oxo-3-phenyl-propyl]amino]-benzoic acid, dilithium salt.

7. The compound of claim 5, (S)-3-[[2-[(hydroxymethylphosphinyl)amino]-1-oxo-3-phenylpropyl]amino]-benzoic acid, dilithium salt.

8. A compound of claim 5 wherein:

$R_1$ is

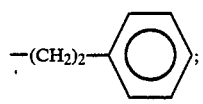

and $R_2$ is

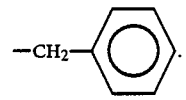

9. The compound of claim 8, 3-[[(S)-2-[[hydroxy(2-phenylethyl)phosphinyl]amino]-1-oxo-3-phenylpropyl]amino]propanoic acid, dilithium salt.

10. A compound of claim 2 wherein:

$R_1$ is

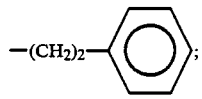

and $R_2$ is methyl.

11. The compound of claim 10, 3-[[(S)-2-[[hydroxy(2-phenylethyl)phosphonyl]amino]-1-oxo-propyl]amino]-propanoic acid, dilithium salt.

12. A pharmaceutical composition useful for reducing blood pressure and producing diuresis and natriuresis as well as treating congestive heart failure, pain, and/or diarrhea in a mammalian host comprising a pharmaceutically acceptable carrier and an endopeptidase inhibiting compound of the formula

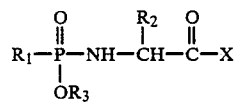

wherein X, $R_1$, $R_2$, and $R_3$ are as defined in claim 1.

13. A pharmaceutical composition useful for reducing blood pressure and producing diuresis and natriuresis as well as treating congestive heart failure, pain, and/or diarrhea in a mammalian host comprising a pharmaceutically acceptable carrier and an endopeptidase inhibiting compound of the formula

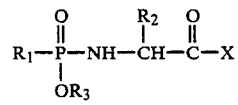

wherein X, $R_1$, $R_2$ and $R_3$ are as defined in claim 2.

* * * * *